United States Patent [19]
Lee et al.

[11] Patent Number: 5,726,204
[45] Date of Patent: Mar. 10, 1998

[54] SUKSDORFIN ANALOGS, COMPOSITIONS THEREOF, AND METHODS FOR MAKING AND USING THEREOF

[75] Inventors: Kuo-Hsiung Lee; Yoshiki Kashiwada; Li Huang; Thomas Tung-Ying Lee, all of Chapel Hill, N.C.; Mark Cosentino, Springfield, Va.; Jim Snider, Hagerstown; Mark Manak, Laurel, both of Md.; Lan Xie, Chapel Hill, N.C.

[73] Assignees: Biotech Research Laboratories, Rockville, Md.; University of North Carolina at Chapel Hill, Chapel Hill, N.C.

[21] Appl. No.: 462,280

[22] Filed: Jun. 5, 1995

Related U.S. Application Data

[63] Continuation of Ser. No. 392,558, Feb. 21, 1995, Pat. No. 5,637,589, which is a continuation-in-part of Ser. No. 235,852, Apr. 29, 1994, abandoned, which is a continuation-in-part of Ser. No. 142,992, Oct. 29, 1993, abandoned.

[51] Int. Cl.$^6$ ............ A61K 31/365; C07D 311/94; C07D 493/06
[52] U.S. Cl. ............ 514/455; 514/460; 549/280; 549/282
[58] Field of Search ............ 549/280, 282; 514/455, 460

[56] References Cited

U.S. PATENT DOCUMENTS

| | | | |
|---|---|---|---|
| 2,980,699 | 4/1961 | Smith et al. | 260/343.2 |
| 5,089,634 | 2/1992 | Powers et al. | 549/285 |
| 5,177,073 | 1/1993 | Gulliya et al. | 514/224.8 |
| 5,324,648 | 6/1994 | Powers et al. | 435/184 |

FOREIGN PATENT DOCUMENTS

| | | |
|---|---|---|
| 3227923 | of 0000 | Japan . |
| 8907939 | 9/1989 | WIPO . |
| 9211850 | 7/1992 | WIPO . |
| 9218123 | 10/1992 | WIPO . |
| 9406787 | 3/1994 | WIPO . |
| 9414789 | 7/1994 | WIPO . |
| 9418188 | 8/1994 | WIPO . |

OTHER PUBLICATIONS

Taylor, et al.; "Kinetic and Mutational Analysis of Human Immunodeficiency Virus Type 1 Reverse Transcriptase Inhibition by Inophyllums, a Novel Class of Non–nucleoside Inhibitors"; *Journal of Biological Chemistry;* vol. 269, No. 9; 6325–6331; Mar. 4, 1994.

Lunney, et al.; "A Novel Nonpeptide HIV–1 Protease Inhibitor: Elucidation of the Binding Mode and Its Application in the Design of Related Analogs"; *J. Med. Chem.;* vol. 37, No. 17; 2664–2677; 1994.

Greenspan et al.; "Could Oxidative Stress Initiate Programmed Cell Death in HIV Infection? A Role for Plant Derived Metabolites Having Synergistic Antioxidant Activity"; *Chemico–Biological Interactions;* vol. 91; 187–197; 1994.

Patil, et al.; "The Inophyllums, Novel Inhibitors of HIV–1 Reverse Transcriptase isolated from the Malaysian Tree, Calophyllum Inophyllum Linn"; *Journal of Medicinal Chemistry;* vol. 36, No. 26; 4131–4138; Dec. 24, 1993.

Boyer, et al.; "Analysis of Nonnucleoside Drug–Resistant Variants of Human Immunodeficiency Virus Type 1 Reverse Transcriptase"; *Journal of Virology;* vol. 67, No. 4; 2412–2420; Apr., 1993.

Zmudzka, et al.; "Activation of the Human Immunodeficiency Virus Promoter by UVA Radiation in Combination with Psoralens or Angelicins"; *Photochemistry and Photobiology;* vol. 58, No. 2; 226–232; 1993.

Hatano, et al.; "Phenolic Constituents of Licorice. II. Structures of Licopyranocoumarin, Licoarylcoumarin and Glisoflavone, and Inhibtory Effects of Licorice Phenolics on Xanthine Oxidase"; *Chem. Pharm. Bull.;* vol. 37, No. 11; 3005–3009; Nov., 1989.

Kashman, et al.; "The Calanolides, a Novel HIV–Inhibitory Class of Coumarin Derivatives from the Tropical Rainforest Tree, Calophyllum Lanigerum"; *J. Med. Chem.;* vol. 35, No. 15; 2735–2743; 1992.

Bourinbaiar, et al.; "Effect of the Oral Anticoagulant, Warfarin, on HIV–1 Replication and Spread"; *AIDS;* vol. 7, No. 1; 129–130; 1993.

Greenspan, et al.; "Oxidative Stress and Apoptosis in HIV Infection: a Role for Plant–Derived Metabolites with Synergistic Antioxidant Activity"; *Immunology Today;* vol. 15, No. 5; 209–213; 1994.

Bourinbaiar, et al.; "Inhibitory Effect of Coumarine on HIV–1 Replication and Cell–Mediated or Cell–Free Viral Transmision"; *Acta Virol.;* vol. 37; 241–250; 1993.

(List continued on next page.)

*Primary Examiner*—Ba K. Trinh
*Attorney, Agent, or Firm*—Sterne, Kessler, Goldstein & Fox P.L.L.C.

[57] ABSTRACT

The present invention is directed to compounds that are analogs of the natural product suksdorfin. Compounds of the present invention include those having Formula I:

wherein $R^1$, $R^2$, $R^3$, $R^4$, $R^5$ and $R^6$ are defined herein. The invention is also directed to methods of making these compounds, pharmaceutical compositions including these compounds and methods of using the compounds to inhibit retroviral infections in cells and tissues of animals. A method for stereoselectively preparing compounds within the scope of the invention by catalytic asymmetric dihydroxylation is also disclosed.

32 Claims, No Drawings

OTHER PUBLICATIONS

Kimura, et al.; "Effects of Active Compounds Isolated From Angelica Shikokiana on Lipid Metabolism in Fat Cells"; *Journal of Ethnopharmacology;* vol. 25; 269–280; 1989.

Nishino, et al.; "Studies on the Anti–Tumor–Promoting Activity of Naturally Occurring Substances. IV. Pd–II [(+) Anomalin, (+) Praeruptorin B], a Saselin–Type Coumarin, Inhibits the Promotion of Skin Tumor Formation by 12–0–Tetradecanoylphorbol–13–Acetate in 7,12–Dimethylbenz [a] Anthracene–Initiated Mice"; *Carcinogenesis;* vol. 11, No. 9; 1557–1561; 1990.

Meyer, et al.; "Plant Antitumor Agents, 21. Flavones, Coumarins, and an Alkaloid from Sargentia Greggli"; *Journal of Natural Products;* vol. 48, No. 6; 952–956; Nov.–Dec., 1985.

Thastrup, et al.; "Inhibition of Human Platelet Aggregation by Dihydropyrano– and Dihydrofuranocoumarins, a New Class of cAMP–Phosphodiesterase Inhibitors"; *Biochemical Pharmacology;* vol. 34, No. 12; 2137–2140; 1985.

Delgado, et al.; "Pyranocoumarins from Arracacia Nelsonii"; *Biochemistry;* vol. 26, No. 4; 1139–1141; 1987.

Baccichetti, et al.; "Photobiological Activity of Certain Pyranocoumarin Derivatives: Potential Agents for the Photochemotherapy of Psoriasis"; *Photodermatology;* vol. 3; 261–270; 1986.

Kashman, et al.; "Additions and Corrections"; *J. Med. Chem.;* vol. 35; 1110; 1992.

Huang et al. *3'4'–DI–O–(–)–Camphanoyl–(+)–CIS–Khellactone and Related Compounds: A New Class of Potent Anti–Hiv Agnets,* Bioorganic and Medicinal Chemistry Letters, vol. 4, No. 4, pp. 593–598, Feb. 23, 1994.

Vichkonova et al, *Antimicrobial and Antiviral Activity of Some natural Coumarins,* Chemical Abstracts vol. 79, No. 19, p. 49, Abstract No. 111980v, Nov. 12, 1973.

Schroeder et al, *Struktur der Visnagane; Synthese von (+–)–Trans–Samidin,* Chemische Berichte, vol. 92, pp. 2338–2363, 1959.

Antonova, et al, *Dihydrosamidin and Visnadin,* Chemical Abstracts, vol. 96, No. 12, p. 407, Abstract No. 96:91638k, Mar. 22, 1982.

Bohlmann et al, *Synthese von Racemischem Lomatin, Columbianetin, Angenomalin und Samidin,* Chemische Berichte, vol. 104, pp. 3229–3233, 1971.

SUKSDORFIN ANALOGS, COMPOSITIONS THEREOF, AND METHODS FOR MAKING AND USING THEREOF

This is a continuation of application Ser. No. 08/392,558 filed Feb. 21, 1995, now U.S. Pat. No. 5,637,589 which is a continuation-in-part of U.S. Ser. No. 08/235,852, filed Apr. 29, 1994, now abandoned which is a continuation-in-part of U.S. Ser. No. 08/142,992, filed Oct. 29, 1993, now abandoned each of which applications is hereby incorporated by reference.

The present application was funded under National Institute of Allergies grant #AI-33066 such that the U.S. Government has certain rights in this invention.

FIELD OF THE INVENTION

The present invention relates to suksdorfin analogs which have been found to be useful in treating viral infections, such as HIV infections, as well as to purifying these analogs.

BACKGROUND OF THE INVENTION

Retroviruses

Retroviruses are small, single-stranded positive-sense RNA viruses. A retroviral particle comprises two identical single-stranded positive sense RNA molecules. Their genome contains, among other things, the sequence for the RNA-dependent DNA polymerase, also known as reverse transcriptase. Many molecules of reverse transcriptase are found in close association with the genomic RNA in the mature viral particle. Upon entering a cell, this reverse transcriptase produces a double-stranded DNA copy of the viral genome, which is inserted into the host cell's chromatin. Once inserted, the viral sequence is called a provirus. Retroviral integration is directly dependent upon viral proteins. Linear viral DNA termini (the LTRs) are the immediate precursors to the integrated proviral DNA. There is a characteristic duplication of short stretches of the hosts DNA at the site of integration.

Progeny viral genomes and mRNAs are transcribed from the inserted proviral sequence by host cell RNA polymerase II in response to transcriptional, regulatory signals in the terminal regions of the proviral sequence, the long terminal repeats or LTRs. The host cell's proteins production machinery is used to produce viral proteins, many of which are inactive until processed by virally encoded proteases. Typically, viral particles bud from the cell surface in a non-lyric manner. Retroviral infection does not necessarily interfere with the normal life cycle of an infected cell or organism. However, neither is it always benign with respect to the host organism. While most classes of DNA viruses can be implicated in tumorigenesis, retroviruses are the only taxonomic group of RNA viruses that are oncogenic. Various retroviruses, such as the Human Immunodeficiency Virus (HIV), which is the etiological agent responsible for acquired immune deficiency syndrome (AIDS) in humans, are also responsible for several very unusual diseases of the immune systems of higher animals.

HIV INFECTION AND AIDS

Human Immunodeficiency Virus (HIV), the etiological agent for AIDS (acquired immune deficiency syndrome), is a member of the lentiviruses, a subfamily of retroviruses. Many retroviruses are well-known carcinogens. HIV per se is not known to cause cancer in humans or other animals, but it does present a formidable challenge to the host. HIV integrates its genetic information into the genome of the host. The viral genome contains many regulatory elements which allow the virus to control its rate of replication in both resting and dividing cells. Most importantly, HIV infects and invades cells of the immune system; it breaks down the body's immune system and renders the patient susceptible to opportunistic infections and neoplasms. The immune defect appears to be progressive and irreversible, with a high mortality rate that approaches 100% over several years.

HIV-1 is trophic and cytopathic for T4 lymphocytes, cells of the immune system which express the cell surface differentiation antigen CD4 (also known as OKT4, T4 and leu3). The viral tropism is due to the interactions between the viral envelope glycoprotein, gp120, and the cell-surface CD4 molecules (Dalgleish, et al., *Nature* 312:763–767, 1984. These interactions not only mediate the infection of susceptible cells by HIV, but are also responsible for the virus-induced fusion of infected and uninfected T cells. This cell fusion results in the formation of giant multinucleated syncytia, cell death, and progressive depletion of CD4 cells in AIDS patients. These events result in HIV-induced immunosuppression and its subsequent sequelae, opportunistic infections and neoplasms.

In addition to CD4+ T cells, the host range of HIV includes cells of the mononuclear phagocytic lineage (Dalgleish et al., supra), including blood monocytes, tissue macrophages, Langerhans cells of the skin and dendritic reticulum cells within lymph nodes. HIV is also neurotropic, capable of infecting monocytes and macrophages in the central nervous system causing severe neurologic damage. Macrophage/monocytes are a major reservoir of HIV. They can interact and fuse with CD4-bearing T cells, causing T cell depletion and thus contributing to the pathogenesis of AIDS.

ANTI-HIV DRUGS

Intensive efforts are currently under way to develop therapies to prevent or intervene in the development of clinical symptoms in HIV-infected individuals. For the most part, efforts have been focused on the use of nucleoside analogue drugs such as AZT (azidothymidine), and on other dideoxynucleoside derivatives such as ddA, ddT, ddI, and ddC. These drugs inhibit the viral enzyme, reverse transcriptase, thereby inhibiting de novo infection of cells. However, once viral infection has been established within a cell, viral replication utilizes host cell enzymes. Thus, drugs which inhibit only reverse transcriptase tend to have limited effects. While the spread of free virus within the organism can be blocked, the mechanisms of syncytium formation and pathogenesis through direct intercellular spread remain. Accordingly, there is a need to provide a new anti-HIV drugs which are not limited to inhibiting reverse transcription as their mechanism of action.

Coumarins and Photoactive Compounds *Lomatium suksdorfii* (Umbelliferae) is distributed on the United States western coast. The roots of several Lomatium species were used medicinally by the Gosiute Indians who called the plant "pia-a-na-tsu" or "great medicine". The oil and a crystalline substance obtained from *L. suksdorfii* were previously found to exhibit antispasmodic and antibacterial activities (Petrihate et al, *J. Amer. Pharm. Assoc.*, 48:423 (1959).

Powers et al, in U.S. Pat. No. 5,089,634, disclose isocoumarins with cationic substituents for use in inhibiting serine proteases with trypsin-like, chymotrypsin-like and elastase-like specificity and their roles as anticoagulant agents and anti-inflammatory agents. Isocoumarin and related heterocyclic compounds represented according to disclosed formula (I) or a pharmaceutically acceptable salt are also disclosed.

Gulliya et al, in U.S. Pat. No. 5,177,073, discloses therapeutic compositions derived from a pre-activated photoactive compound and a conveyor for destroying tumor or other pathogenic biological contaminants infecting animal body tissues, wherein the conveyor can be a matrix support or an antibody. The activation of the photoactive compound is used to produce the pre-activated photoactive compound retaining therapeutic activity subsequent to activation. Such photodynamic therapy involves the administration of one or more photoactive agents to a subject to be treated followed by exposing the specific target location or target organ of the subject to light. The photoactive compound is required to have one or more chromophores capable of absorbing light energy and capable of being coupled to a matrix support or antibody.

Call and Green, *Proc. Montana. Acad. Sci.* 16:49 (1956) describe methods for activation of pyronocoumarin derivatives.

It is well known that one member of a group of stereoisomers has very potent activity, while other member(s) of the group may be useless for the same purpose. Often, mixtures of stereoisomers have much lower activity than is useful. For compounds having stereoisomer, it is important to be able to prepare the useful stereoisomer apart from the other stereoisomers, as separation of stereoisomers is often difficult and inefficient.

Sharpless and his co-workers have extensively researched the asymmetric dihydroxylation of olefins since 1988, as reported in Jacobsen et al., *J. Am. Chem. Soc.*, 1988, 110, 1968–1970. Substantial progress has been made in the development of ligands that generate ever higher levels of enantioselectivityz: Crispino et al., *J. Org. Chem.*, 1993, 58, 3785–3786; Amberg et al., *J. Org. Chem.*, 1993, 58, 844–849, Sharpless et al., *J. Org. Chem.*, 1992, 57, 2768–2771. A variety of olefins have been investigated with very good results. Unfortunately, a high level of enantioselectivity in asymmetric dihydroxylation of a styrene-like olefin contained in a six-membered ring fused with benzene has not been reported.

Citation of documents herein is not intended as an admission that any of the documents cited herein is pertinent prior art, or an admission that the cited document is considered material to the patentability of the claims of the present application. All statements as to the date or representation as to the contents of these documents is based on the information available to the applicant and does not constitute any admission as to the correctness of the dates or contents of these documents.

SUMMARY OF THE INVENTION

The present invention is intended to overcome one or more deficiencies of the related art.

The present invention is intended to also provide suksdorfin analogs which have anti-viral activity and/or anti-retroviral activity, such as anti-HIV activity, in vitro, in situ and/or in vivo, as well as preparing these suksdorfin analogs.

The present invention provides suksdorfin analogs according to the general formula (G-1) which can be used to inhibit retroviral growth, replication, binding and/or metabolism, and/or to treat a retroviral infection or related symptoms.

The present invention also provides a process for purifying suksdorfin or suksdorfin analogs having anti-HIV activity from a sample containing such a compound, such as, but not limited to, the fruit of the plant *Lomatium suksdorfi*, the method comprising: (a) extracting sample preparations with hexane to provide active fractions; (b) centrifuging the active fractions at least once; (c) recovering the supernatant; and (d) purifying the precipitate by silica gel chromatography to recover the suksdorfin analog, thereby purifying the protein.

The present invention is also directed to synthetic methods for making suksdorfin analogs according to formula (I) or formula (II), and particularly to making specific stereoisomers of suksdorfin analogs.

The invention is also directed to a method for treating a subject infected with HIV-1 by administering at least one suksdorfin analog, optionally in combination with any one or more of the known anti-AIDS therapeutics or an immunostimulant.

The treatment methods of the invention also include administering to a subject infected with HIV-1 a conjugate of a suksdorfin derivative with soluble CD4, CD4 derivatives, antibodies specific for CD4, or HIV-coded glycoproteins such as gp120 and gp41, or antibodies thereto.

Other features, advantages, embodiments, aspects and objects of the present invention will be clear to those skilled in the areas of relevant art, based on the description, teaching and guidance presented herein.

DETAILED DESCRIPTION OF THE PREFERRED EMBODIMENTS

An example of a suksdorfin analog according to the present invention is a suksdorfin analog according to formula (I).

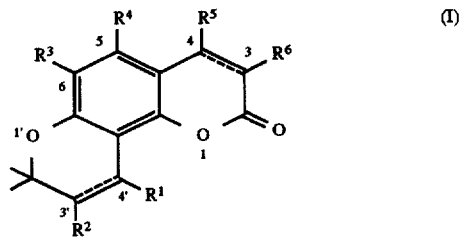

wherein $R^1$, $R^2$ are either cis-β or cis-α, or trans-3'-α or trans-3'-β-oriented, wherein $R^1$, $R^2$, $R^3$ and $R^4$ are H, $C_{1-10}$ alkyl, $C_{1-10}$ O-acyl, O-alkyl, amide, or $CH_2COOR'$, where R' is $C_{1-10}$ alkyl or acyl; $R^5$ is H, $C_{1-10}$ alkyl, $C_{1-10}$ acyl, $CF_3$, amide or $CH_2COOR^7$, where $R^7$ is $C_{1-10}$ alkyl, acyl or amide; and $R^6$ is H, halogen, $C_{1-10}$ alkyl, or $CH_2CH_2NCOOR^8$, where $R^8$ is C1-10 alkyl; C3 or C4 can be bound by a single or double bond; $R^1$ or $R^2$ can be cis-β or cis-α, or trans-3'-α or trans-3'-β-oriented.

Another non-limiting example of a suksdorfin analog of the present invention is a suksdorfin analog according to formula II.

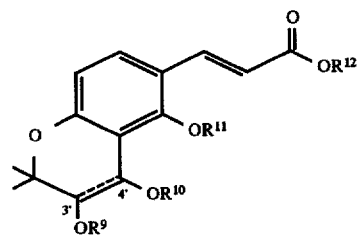

wherein $R^9$, $R^{10}$, $R^{11}$ and $R^{12}$ are either cis-β or cis-α, or trans-3'-α or trans-3'-β-oriented, wherein $R^9$, $R^{10}$, $R^{11}$ and $R^{12}$ are H, $C_{1-10}$ acyl, amide-acyl, amide-alkyl or $CH_2OOR'$, where R' is $C_{1-10}$ alkyl or $C_{1-10}$ acyl.

Another example of a suksdorfin analog of the present invention is a suksdorfin analog according to formula III.

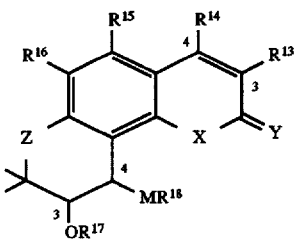

(III)

wherein M is O or NH; X, Y and Z=O, NH or S; $R^{13}$, $R^{14}$, $R^{15}$, and $R^{16}$, are each H, halogen, OH, O-alkyl, O-acyl, $NH_2$, NH-alkyl, N-(alkyl)$_2$, $CF_3$, $OCF_3$ or $CH_2CONH$-alkyl; $R^{17}$ and $R^{18}$, are each H, $C_{1-10}$ alkyl, $C_{1-10}$ acyl, aryl, $COCF_3$, amide or $CH_2COOR^{19'}$, where $R^{19'}$ is $C_{1-10}$ alkyl, $C_{1-10}$ acyl, aryl or (+)-camphanoyl or (−)-camphanoyl; and wherein the bond between C3 and C4 can be double or single. Configurations at 3' or 4' can be (R) or (S). $R^{17}$ and $R^{18}$ can each be cis-β or cis-α, or trans-3'-α or trans-3'-β-oriented.

Non-limiting examples of suksdorfin analogs according to formula (I) include the following combinations of $R^1$, $R^2$, $R^3$, $R^4$, $R^5$ and $R^6$.

(I-A) $R^1=R^2=R^3=R^4=R^5=R^6=H$
(I-B) $R^1=R^2=R^4=R^5=R^6=H$, $R^3=$O-alkyl
(I-C) $R^1=R^2=R^3=R^4=R^6=H$, $R^5=$alkyl, $CF_3$, $CH_2CO$ alkyl
(I-D) $R^1=R^2=R^3=R^4=R^6=H$, $R^5=CH_2CONH$-alkyl
(I-E) $R^1=R^2=$O-acyl, $R^3=R^4=R^5=R^6=H$
(I-F) $R^1=R^2=$O-acyl, $R^3=$O-alkyl, $R^4=R^5=R^6=H$
(I-G) $R^1=R^2=$O-acyl, $R^3=R^4=R^6=H$, $R^5=$alkyl, $CF_3$, $CH_2COO$-alkyl
(I-H) $R^1=R^2=$O-acyl, $R^3=R^4=R^6=H$, $R^5=CH_2COHN$-alkyl
(I-J) $R^1=R^2=$O-acyl, $R^3=R^4=H$, $R^5=$alkyl, $R^6=$halogen or $CH_2CH_2N$-alkyl
(I-K) $R^3=R^4=R^5=R^6=R^1=H$, $R^2=$—O-alkyl, $OCOCH(CH_3)C_2H_5$
(I-L) $R^3=R^4=R^5=R^6=R^2=H$, $R^1=$—O-alkyl, $OCOCH(CH_3)C_2H_5$
(I-M) $R^3=R^4=R^5=R^6=H$, $R^1=R^2=$—O-alkyl
(I-N) $R^3=R^4=R^5=R^6=H$, $R^1=R^2=OCOCH(CH_3)C_2H_5$
(I-O) $R^3=R^4=R^5=R^6=H$, $R^1=R^2=OCOCH_2CH(CH_3)_2$
(I-P) $R^3=R^4=R^5=R^6=H$, $R^1=R^2=$

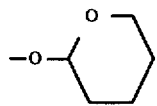

(I-Q) $R^3=R^4=R^5=R^6=H$, $R^1=$—O-acyl, $OCOCH(CH_3)C_2H_5$
(I-R) $R^3=R^4=R^5=R^6=H$, $R^1=OCOCH(CH_3)C_2H_5$, $R^2=$—O-acyl
(I-S) $R^3=R^4=R^5=R^6=R^2=H$, $R^1=$—O-acyl
(I-T) $R^3=R^4=R^5=R^6=R^2=H$, $R^1=OCOCH_2CH(CH_3)_2$
(I-U) $R^2=R^3=R^4=R^5=R^6=H$, $R^1=$—O—$CH_2$-Ø, where Ø=phenyl
(I-V) $R^2=R^3=R^4=R^5=R^6=H$, $R^1=$OMe (I-W) $R^2=R^3=R^4=R^5=R^6=H$, $R^1=$

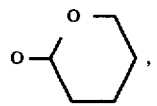

(I-X) $R^3=R^4=R^5=R^6=H$, $R^1=$OMe, $R^2=$—O-acyl
(I-Y) $R^3=R^4=R^5=R^6=H$, $R^1=$ $R^2=OCOCH_2CH(CH_3)_2$ (I-Z) $R^3=R^4=R^5=R^6=H$, $R^1=OCH_2$-Ø, $R^2=$—O-acyl Non-limiting examples of suksdorfin analogs according to formula (II) include the following combinations of $R^9$, $R^{10}$, $R^{11}$ and $R^{12}$.

(II-A) $R^9=R^{10}=R^{11}=R^{12}=H$
(II-B) $R^{10}=R^{11}=R^{12}=H$, $R^9=$alkyl
(II-C) $R^9=R^{10}=R^{11}=H$, $R^{12}=$alkyl, $CF_3$, or $CH_2CO$-alkyl
(II-D) $R^9=R^{10}=R^{11}=H$, $R^{12}=CH_2CONH$-alkyl
(II-E) $R^9=R^{10}=$acyl, $R^{11}=R^{12}=H$
(II-F) $R^9=R^{10}=$acyl, $R^{11}=$-alkyl, $R^{12}=H$
(II-G) $R^9=R^{10}=$acyl, $R^{11}=H$, $R^{12}=$alkyl, $CF_3$, $CH_2COO$-alkyl
(II-H) $R^9=R^{10}=$acyl, $R^{11}=H$, $R^{12}=CH_2CONH$-alkyl
(II-J) $R^9=R^{10}=$acyl, $R^{11}=H$, $R^{12}=$alkyl,
(II-K) $R^{11}=R^{12}=R^9=H$, $R^{10}=$alkyl, $COCH(CH_3)C_2H_5$
(II-L) $R^{10}=R^{11}=R^{12}=H$, $R^9=$alkyl, $COCH(CH_3)C_2H_5$
(II-M) $R^{11}=R^{12}=H$, $R^9=R^{10}=$acyl
(II-N) $R^{11}=R^{12}=H$, $R^9=R^{10}=COCH(CH_3)C_2H_5$
(II-O) $R^{11}=R^{12}=H$, $R^9=R^{10}=COCH_2CH(CH_3)_2$
(II-P) $R^{11}=R^{12}=H$, $R^9=R^{10}=$

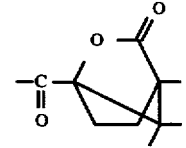

(II-Q) $R^{11}=R^{12}=H$, $R^9=$acyl, $R^{10}=COCH(CH_3)C_2H_5$
(II-R) $R^{11}=R^{12}=H$, $R^9=COCH(CH_3)C_2H_5$, $R^{10}=$acyl
(II-S) $R^{11}=R^{12}=R^{10}=H$, $R^9=$acyl
(II-T) $R^{11}=R^{12}=R^{10}=H$, $R^9=COCH_2CH(CH_3)_2$
(II-U) $R^{10}=R^{11}=R^{12}=H$, $R^9=CH_2$Ø, where Ø=phenyl
(II-V) $R^{10}=R^{11}=R^{12}=H$, $R^9=$Me
(II-W) $R^{10}=R^{11}=R^{12}=H$, $R^9=$

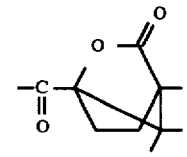

(II-X) $R^{10}=R^{11}=R^{12}=H$, $R^9=$Me, $R^{10}=$acyl (II-Y) $R^{10}=R^{11}=R^{12}=H$, $R^9=$

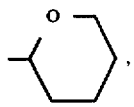, $R^{10}=COCH_2CH(CH_3)_2$ (II-Z) $R^{10}=R^{11}=R^{12}=H$, $R^9=CH_2-\emptyset$, $R_{10}=$acyl Non-limiting examples of suksdorfin analogs according to formula (III) include the following combinations $R^{13}$, $R^{14}$ of $R^{15}$, $R^{16}$, $R^{17}$, $R^{18}$, X, Y, Z and M.

(III-A) $R^{13}=R^{14}=R^{15}=R^{16}=R^{17}=R^{18}=H$, $M=Y=Z=O$, $X=NH$ (III-B) $R^{13}=R^{14}=R^{15}=R^{16}=R^{18}=H$, $R^{17}=$alkyl, $M=Y=Z=O$, $X=NH$ (III-C) $R^{14}=R^{15}=R^{16}=R^{17}=R^{18}=H$, $R^{13}=O$-alkyl, $M=Y=Z=O$, $X=NH$ (III-D) $R^{14}=R^{15}=R^{16}=R^{17}=R^{18}=H$, $R^{13}=O-CH_2CONH$-alkyl, $M=Y=Z=O$, $X=NH$ (III-E) $R^{17}=R^{18}=$acyl, $R^{13}=R^{14}=R^{15}=R^{16}=H$, $M=Y=Z=O$, $X=NH$ (III-F) $R^{17}=R^{18}=$acyl, $R^{16}=O$-alkyl, $R^{13}=R^{14}=R^{15}=R^{16}=H$, $M=Y=Z=O$, $X=NH$ (III-G) $R^{17}=R^{18}=$acyl, $R^{13}=O$-alkyl, $O-CF_3$, $O-CH_2COO$-alkyl, $R^{14}=R^{15}=R^{16}=H$, $M=Y=Z=O$, $X=NH$ (III-H) $R^{17}=R^{18}=$acyl, $R^{14}=R^{15}=R^{16}=H$, $R^{13}=O-CH_2CONH$-alkyl, $M=Y=Z=O$, $X=NH$ (III-J) $R^{17}=R^{18}=$acyl, $R^{15}=R^{16}=H$, $R^{13}=$halogen or $CH_2CH_2N$-alkyl, $R^{14}=$alkyl, $M=Y=Z=O$, $X=NH$ (III-K) $R^{13}=R^{14}=R^{15}=R^{16}=R^{18}=H$, $R^{17}=$alkyl or $COCH(CH_3)C_2H_5$, $M=Y=Z=O$, $X=NH$ (III-L) $R^{13}=R^{14}=R^{15}=R^{16}=R^{17}=H$, $R^{18}=$alkyl or, $COCH(CH_3) C_2H_5$, $M=Y=Z=O$, $X=NH$ (III-M) $R^{13}=R^{14}=R^{15}=R^{16}=H$, $R^{17}=R^{18}=$acyl, $M=Y=Z=O$, $X=NH$ (III-N) $R^{13}=R^{14}=R^{15}=R^{16}=H$, $R^{17}=R^{18}=COCH(CH_3)C_2H_5$, $M=Y=Z=O$, $X=NH$ (III-O) $R^{13}=R^{14}=R^{15}=R^{16}=H$, $R^{17}=R^{18}=COCH_2CH(CH_3)_2$, $M=Y=Z=O$, $X=NH$ (III-P) $R^{13}=R^{14}=R^{15}=R^{16}=H$, $R^{17}=R^{18}=$

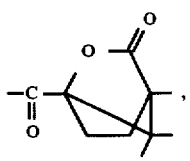, $M=Y=Z=O$, $X=NH$ (III-Q) $R^{13}=R^{14}=R^{15}=R^{16}=H$, $R^{17}=$acyl, $R^{18}=COCH(CH_3)C_2H_5$, $M=Y=Z=O$, $X=NH$ (III-R) $R^{13}=R^{14}=R^{15}=R^{16}=H$, $R^{18}=COCH(CH_3)C_2H_5$, $R^{17}=$acyl, $M=Y=Z=O$, $X=NH$ (III-S) $R^{13}=R^{14}=R^{15}=R^{16}=R^{17}=H$, $R^{18}=$acyl, $M=Y=Z=O$, $X=NH$ (III-T) $R^{13}=R^{14}=R^{15}=R^{16}=R^{17}=H$, $R^{18}=COCH_2CH(CH_3)_2$, $M=Y=Z=O$, $X=NH$ (III-U) $R^{13}=R^{14}=R^{15}=R^{16}=R^{17}=H$, $R^{18}=CH_2\emptyset$, where $\emptyset=$phenyl, $M=Y=Z=O$, $X=NH$ (III-V) $R^{13}=R^{14}=R^{15}=R^{16}=R^{17}=H$, $R^{18}=Me$, $M=Y=Z=O$, $X=NH$ (III-W) $R^{13}=R^{14}=R^{15}=R^{16}=R^{17}=H$, $R^{18}=$

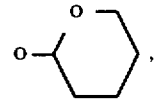, $M=Y=Z=O$, $X=NH$ (III-X) $R^{13}=R^{14}=R^{15}=R^{16}=H$, $R^{18}=Me$, $R^{17}=$acyl, $M=Y=Z=O$, $X=NH$ (III-Y) $R^{13}=R^{14}=R^{15}=R^{16}=H$, $R^{18}=$

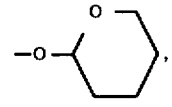, $R^{17}=COCH_2CH(CH_3)_2$, $M=Y=Z=O$, $X=NH$ (III-Z) $R^{13}=R^{14}=R^{15}=R^{16}=H$, $R^{18}=CH_2-\emptyset$, $R^{17}=$acyl, $M=Y=Z=O$, $X=NH$ Such suksdorfin analogs have been unexpectedly discovered to have anti-retroviral activity, thus providing suitable compounds and compositions for treating retroviral infections, optionally with additional pharmaceutically active ingredients, such as anti-retroviral, anti-HIV, and/or immuno-stimulating compounds or antiviral antibodies or fragments thereof.

By the term "anti-retroviral activity" or "anti-HIV activity" is intended the ability to inhibit at least one of (1) retroviral attachment to cells, (2) viral entry into cells, (3) cellular metabolism which permits viral replication, (4) inhibition of intercellular spread of the virus, (5) synthesis and/or cellular expression of viral antigens, (6) activity of virus-coded enzymes (such as reverse transcriptase and protease), and/or (7) any known retroviral or HIV pathogenic actions, such as, for example, immunosuppression. Thus, any activity which tends to inhibit any of these mechanisms is "anti-retroviral activity" or "anti-HIV activity."

The present invention also provides a process for purifying suksdorfin analogs having anti-HIV activity from a sample containing such a compound, such as, but not limited to, the fruit of the plant *Lomatium suksdorfi*, the method comprising: (a) extracting sample preparations with hexane to provide active fractions; (b) centrifuging the active fractions at least once; (c) recovering the supernatant; and (d) purifying the precipitate by silica gel chromatography to recover the suksdorfin analog, thereby purifying the protein.

The present invention also provides alternative synthetic methods for obtaining suksdorfin analogs according to formula (I) or formula (II).

The following scheme 1 provides one set of alternative synthetic steps for producing compounds synthesis of suksdorfin analogs according to formula (I), based on a synthesis of seselin (2) from 7-hydroxy coumarin 1.

The construction of the pyran ring from commercially available 7-hydroxycoumarin (1) involved two steps (1 and 2), which have been described, e.g. by Hlubucek, et al. *Aust. J. Chem.* 24:2347 (1971) the contents of which is incorporated entirely herein by reference. The crude product of the first step can be used directly in the next rearrangement reaction, which will produce seselin (2) in good yield. Seselin can then be used as the starting material for the synthesis of other pyranocoumarin derivatives as presented in Scheme 1, as further described herein, using at least one intermediate compounds designated compounds 3–7, to produce suksdorfin analogs of the present invention, non-limiting as examples of compounds according to formula (I), e.g., as analogs designated compounds 8–11 in scheme 1 and 3; 4'-di-0-acyl cis-khellactone derivatives designated 12–21 in Scheme 1.

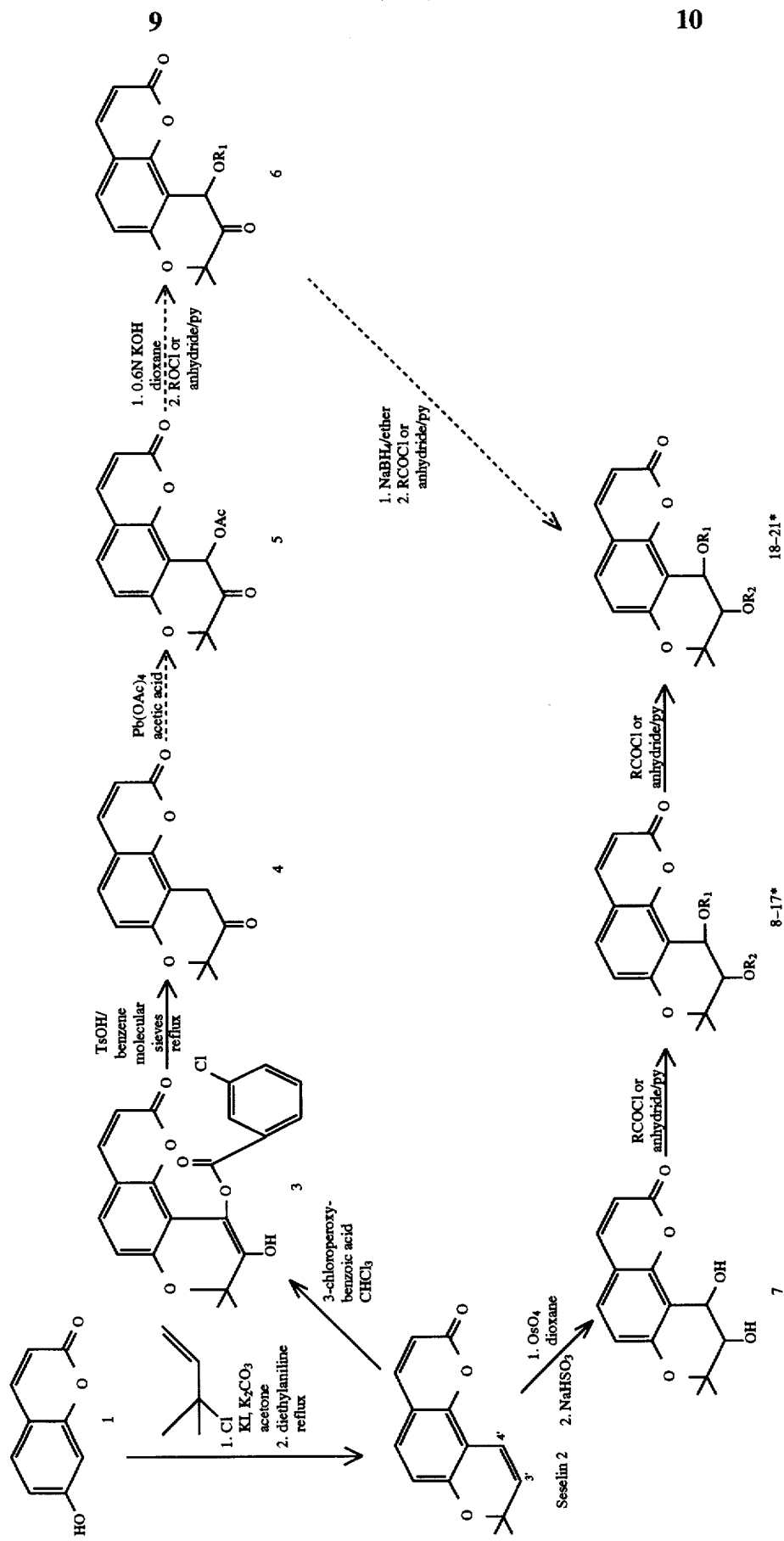

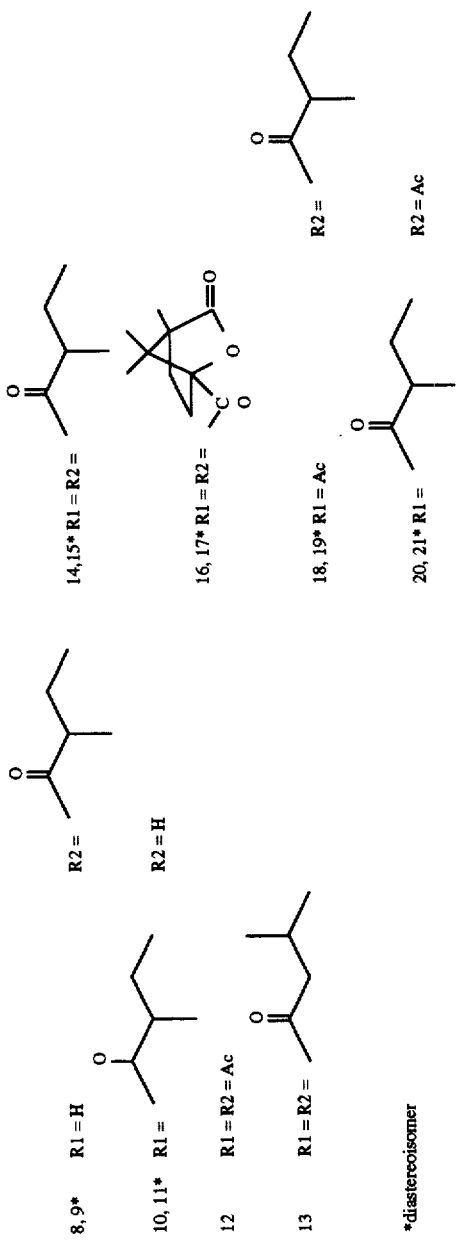

Asymmetric Synthesis of Suksdorfin Analogues

3',4'-di-O-camphanoyl-(+)-cis-khellactone (DCK) has three stereoisomers, as shown below:

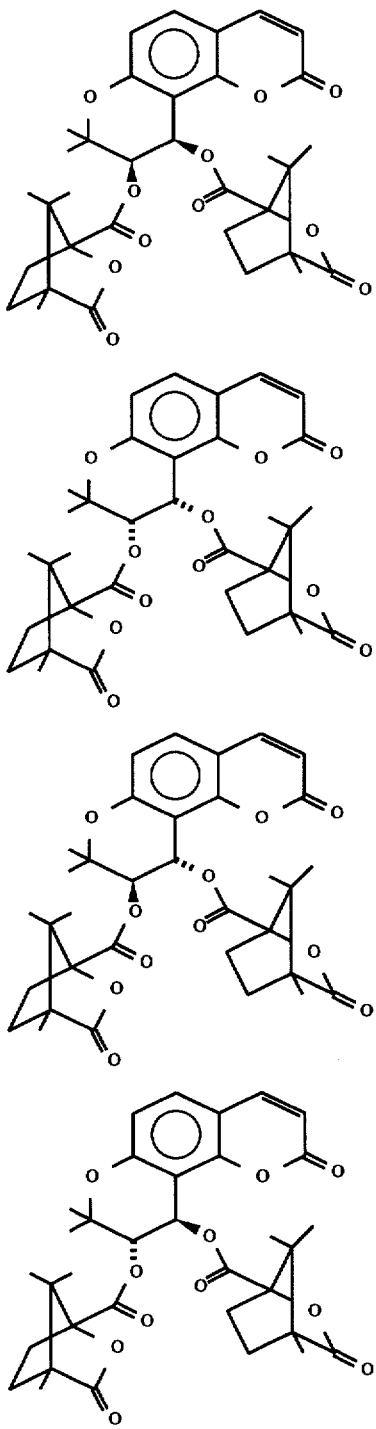

Compound 1B above demonstrated extremely potent inhibitory activity against HIV-1 replication in H9 lymphocyte cells, with an $EC_{50}$ value of 0.00041 uM and a therapeutic index range of >78,049 but <390,244. Compound 1B was more potent than AZT as an anti-HIV agent in this assay. However, compound 2B, the (−)-cis-diastereoisomer of compound 1B, as well as the trans-khellactones with the same acyl groups (compounds 3B and 4B), exhibited much lower anti-HIV activity than compound 1B. These results indicated that a specific configuration in the DCK molecule is very important for its bioactivity.

DCK is synthesized asymmetrically by catalytic asymmetric dihydroxylation of seselin (compound 5B), a synthetic intermediate of DCK. In the initial synthetic route, seselin was oxidized with $OsO_4$ to give racemic cis-dihydroxy-khellactone:

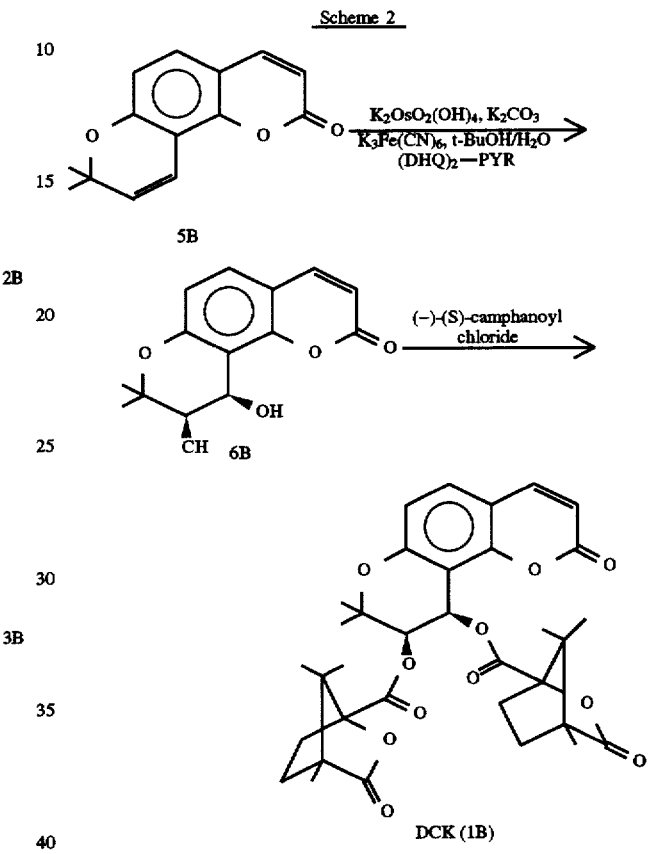

As shown in a representative reaction in Scheme 2, 57 mg, 0.25 mmol of seselin, compound 5B, which was prepared according to Hlubuek et al., *Aust. J. Chem.* 1971, 62, 2347–2354, was added to a well-stirred solution of 150 mg, 0.75 mmol of $K_3Fe(CN)_6$, 105 mg, 0.75 mmol $K_2CO_3$, 1.9 mg, 2% mmol $K_2OsO_2(OH)_4$, and 4.4 mg, 2% mmol 2,5-diphenyl-4,6-bis(9-O-dihydroquinyl)pyrimidine in 5 mL of aqueous t-butyl alcohol (1:1 by volume) at 0° C. The reaction progress was monitored by TLC for four days, at which time the turnover rate of asymmetric dihydroxylation was approximately 75%. Then, one gram of $Na_2S_2O_5$ was slowly added and the suspension was warmed to room temperature for one half hour. The mixture was extracted with $CH_2Cl_2$ and the combined organic layers were dried over $MgSO_4$ and concentrated. The crude cis-diol product, compound 6B, was dried in vacuo and was directly esterified with (−)-(S)-camphanoyl chloride compound 7B, in pyridine at room temperature for 24 hours without further purification. The yield of the mixture of cis-dicamphanoyl khellactones, compounds 1B and 2B, was 68%, calculated from seselin. Compound 1B was the predominant enantiomer, and the extent of enantiomeric excess (ee %) was 86%.

Several different chiral ligands were used in catalytic asymmetric dihydroxylation of seselin in order to obtain optimal enantioselectivity. The results are summarized in Table 1. Different ligands result in different major enantiomers and 33% values under the same conditions of asymmetric dihydroxylation. The DHQD-R type ligands produced primarily the alpha,alpha-cis-diol with S,S configuration (entries 1–4). In contrast, DHQ-R type ligands gave beta,beta-diol, with R,R configuration as the main product (entries 5–12). Different R groups in ligands of the same type can result in different ee % values, as shown by entries 1 and 3. Among the ligands used, (DHQD)$_2$-PYR gave the highest stereoselectivity (entries 4, 11, 12).

TABLE 1

Enantiomeric Excesses (ee %) of Seselin 5 from Catalytic Asymmetric Dihydroxylation with Various DHQD-R and DHQ-R ligands

| entry | Ligand[a] | T (°C.) | time (day) | ee %[a] | config.[b] | t.r. %[c] |
|---|---|---|---|---|---|---|
| 1 | DHQD-CLB | 0 | 4 | 30 | S, S | 75 |
| 2 | DHQD-PHN | r.t. | 1 | 61 | S, S | 75 |
| 3 | DHQD-PHN | 0 | 4 | 67 | S, S | 75 |
| 4 | (DHQD)$_2$-PYR | 0 | 1 | 80 | S, S | 60 |
| 5 | DHQ-PHN | r.t. | 1 | 15 | R, R | 75 |
| 6 | DHQ-PHN | 0 | 4 | 59 | R, R | 75 |
| 7 | DHQ-CLB | r.t. | 1 | 15 | R, R | 75 |
| 8 | DHQ-CLB | 0 | 4 | 50 | R, R | 75 |
| 9 | DHQ-MEQ | r.t. | 2 | 34 | R, R | 81 |
| 10 | DHQ-MEQ | 0 | 1 | 50 | R, R | 62 |
| 11 | (DHQ)$_2$-PYR | 0 | 1 | 86 | R, R | 58 |
| 12 | (DHQ)$_2$-PYR | 0 | 2.5 | 86 | R, R | 85[d] |

[a]Eantioneric excesses were determined by $^1$HNMR analysis of the bis-(−)-camphanic esters, 1 and 2.
[b]THe absolute configuration of the diols were determined by literature comparison.[11]
[c]The turnover rates were calculated from the recovered olefin 5.
[a]THe ligands are available from Aldrich.

It was found that reaction temperature is also an important factor in the reaction rate and enantioselectivity. The asymmetric dihydroxylation of seselin requires up to four days to reach a turnover rate of 75% at 0° C. If the reaction temperature is raised to room temperature, without other changes in the conditions, the reaction rate is faster and reaction time may be shortened to one day. Unfortunately, with increased temperature the enantioselectivity of the reaction may also drop (cf. entries 2&3, 5&6, 7&8, and 9&10). When a catalyst, such as methanesulfonamide, is added, the turnover rate of seselin at temperatures from about −10° C. to about 10° C. is improved, as shown by entry 12.

The 3',4'-di-O-acyl-cis-khellactone derivatives (12–21) can be prepared by other routes e.g., as presented in scheme 1. In another route, seselin (2) can be functionalized at the 3',4'positions by oxidation with m-chloroperoxybenzoic acid to give the (±)-3'-hydroxy-4'-O-acyl derivative 3 (Schroeder et al, Chem. Ber. 92, 2388, (1959), entirely incorporated herein by reference). Tosic acid catalyzed dehydration transformed compound 3 to an optically inactive 3-keto derivative compound 4 (Willette et al J. Pharm. Sci. 51, 149 (1962), entirely incorporated by reference). According to a disclosed method of procedure (e.g., as presented S. N. Shanbhag et al Tetrahedron, 21:3591 (1965), entirely incorporated herein by reference), treatment of compound 4 with lead tetraacetate in acetic acid can yield the racemic 5. After saponification and reesterification at C-4' to give a 3'-keto-4'-O-acyl intermediate compound 6, the ketone can be reduced to an hydroxyl group with NaBH$_4$ (Shanbhag, supra). Further esterification of this (±)-mono ester khellactone with RCOCl or (RCO)$_2$O can furnish the desired (±)-di-O-acyl-khellactone derivatives followed by careful chromatographic separation of their cis racemic mixture to provide compounds 8–21 as presented in scheme 1, or other compounds according to Formula I of the present invention.

In yet another route, e.g., as presented in Scheme 1, seselin compound 2 can be oxidized with OsO$_4$ to give the cis-khellactone intermediate compound 7 in good yield (Schroeder et al, supra). The 3',4'-diester-cis-khellactone compounds 12–17, in which the two ester groups at 3' and 4' are identical, can be produced using standard esterification conditions. However, by using equal molar reagents and mild reaction conditions, selective esterification can be achieved giving the 3'-mono compounds 8 and 9 and the 4'-mono ester khellacetone compounds 10 and 11 in a mixture with the diesters. Separation and further esterification of these mono ester compounds 8–11, using acetic anhydride, can yield the desired (±)-3',4'-di-O-acyl-cis-khellactone derivative compounds 18–21, which have different ester moieties at the 3' and 4' positions. This method can have fewer steps and can give better yields than route 1, through compound 4. However, route 2 can be more expensive and require more extensive safety precautions.

Suksdorfin analogs according to formula (I) of the present invention can be synthesized as jatamansinol derivatives according to Scheme 3, e.g., using published method steps (e.g., Murry et al Tetrahedron letters, entirely incorporated herein by reference 27:4901 (1971)). For example, a phenyl group can be introduced at C-8 of 7-hydroxycoumarin compound 1 in a three-step sequence, which involves a Claisen rearrangement. Under slightly acidic conditions, cyclization of intermediate compound 23 can furnish jatamansinol compound 24. Using standard esterification conditions, (±)-3'-O-acyl-jatamansinol derivative compounds 25 and/or 26 can be synthesized in recoverable amounts.

Scheme 3.
Synthesis of 3'jatamansinol derivatives

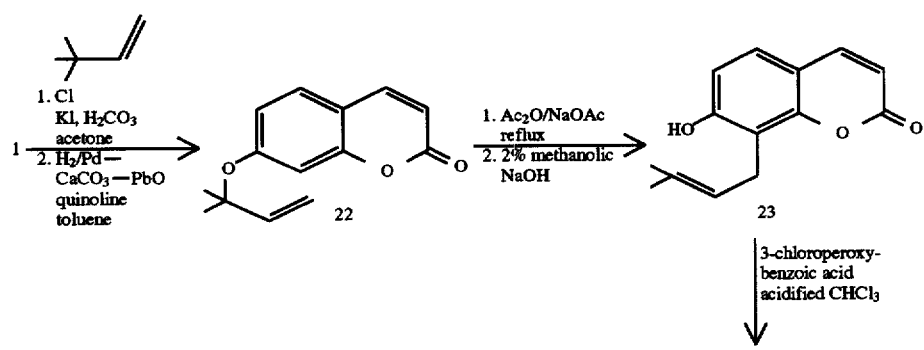

-continued
Scheme 3.
Synthesis of 3'-jatamansinol derivatives

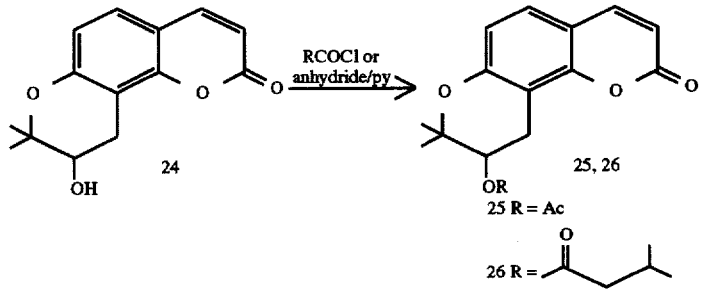

(±)-3',4'-Di-O-acyl-trans-khellactone derivatives and 3'-O-alkyl-4'-O-acyl-trans-khellactone derivative compounds according to formula (I) can be prepared according to Scheme 3.

Preparation of the 3',4'-trans derivatives proceeds from intermediate compound 3A. Compound 3A can be esterified by treatment with the appropriate acyl chloride or acid anhydride to produce the 3',4'-di-O-acyl-trans-khellactone compounds 27,28,33, and 34. Reaction of compound 3A with various alkylating reagents (e.g., MeI, benzyl bromide, dihydropyran) can give the 3'-O-alkyl intermediate compounds 29–32*. Saponification of these compounds can yield the 3'-O-alkyl-4'-hydroxy derivative compounds 35–38. After esterification with an acyl chloride or acid anhydride, the (±)-3'-O-alkyl-4'-O-acyl-trans-khellactone derivatives 39–42 can be synthesized, as presented in scheme 4.

Scheme 4.
Syntheses of 3',4'-trans-khellactone and benzodihyropyran derivatives

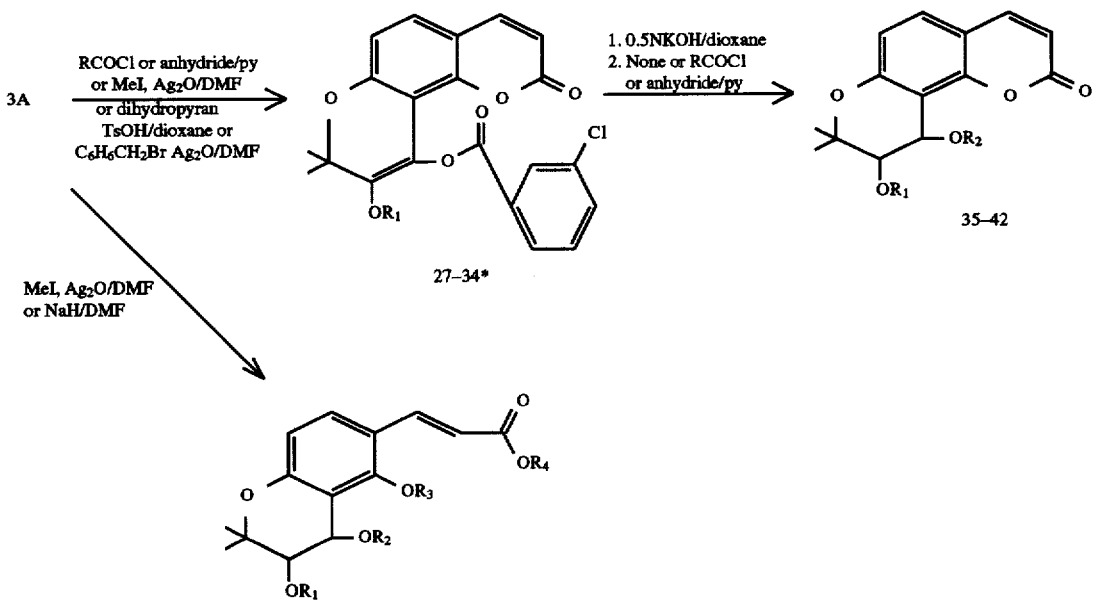

-continued
Scheme 4.
Syntheses of 3',4'-trans-khellactone and benzodihyropyran derivatives

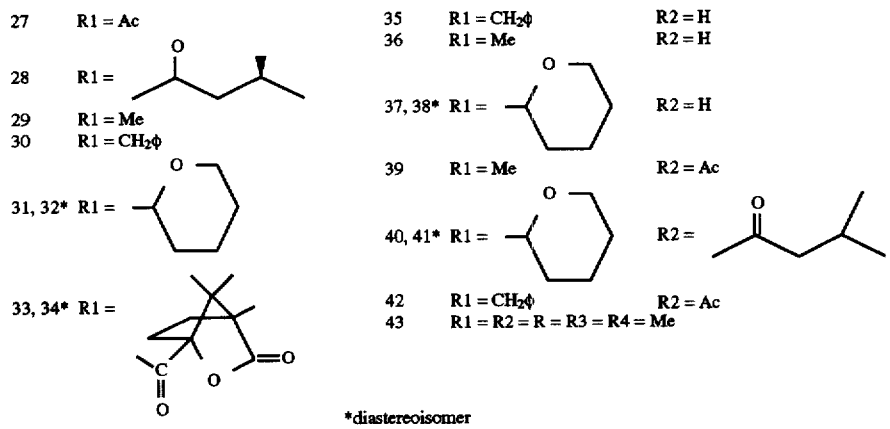

*diastereoisomer

Alternatively (±)-Benzodihydropyran derivatives according to formula (II) can be synthesized according to Scheme 3. The lactone ring in compound 3A or in the 3',4'-di-0-acyl-trans derivatives can be abolished by using a known hydrolysis method step (s) to give (±)-benzodihydropyran compound 43 according to formula (II). The base (KOH, $Ag_2O$, or NaH) cleaves the lactone ring and the ester groups. The free acid or the hydroxyl groups can then undergo alkylation in MeOH or by MeI; to provide suksdorfin analogs according to formula (II) of the presented invention.

Optically pure ester derivative compounds 8–11, 14–21, 33 and 34 according to formula (I) can be obtained using an optically active acyl chloride or acid anhydride as presented in scheme 3. The products are diastereoisomers, which can be separated with repeated chromatography.

Formula (III):

Compounds, represented by formula (III), can be prepared from the following commercially available starting materials 34 and 35, according to the procedures as for preparing compounds according to formula (I) as presented herein.

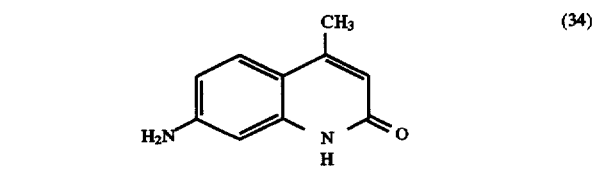

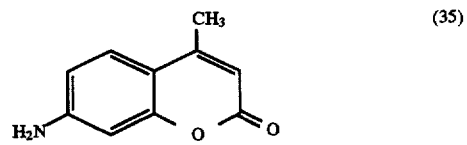

The following starting materials are also prepared by the procedure described in the literature (E. A. Clarke and M. F. Grundon, *J. Chem. Soc.*, 1964,348), which can also be used to prepare compounds according to formula (III), according to known method steps.

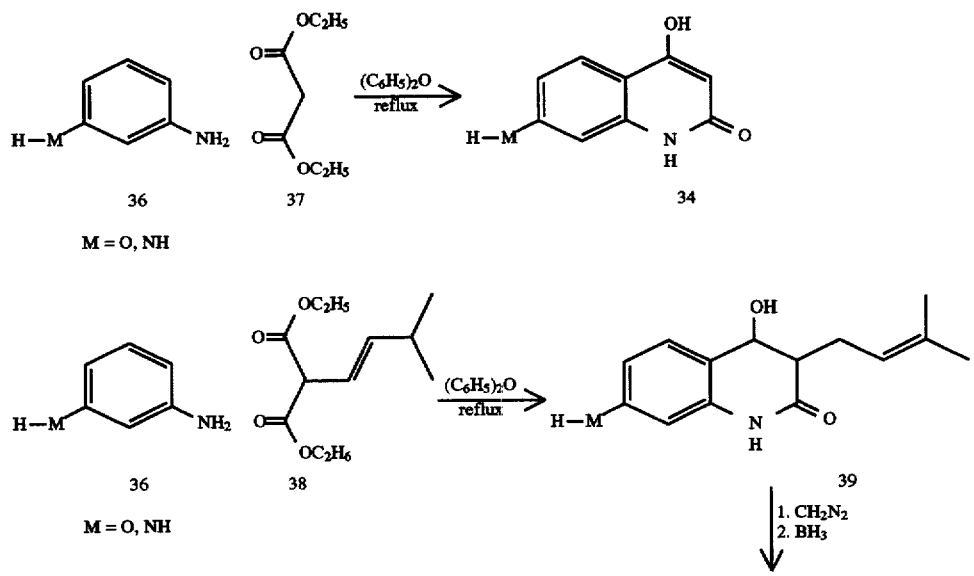

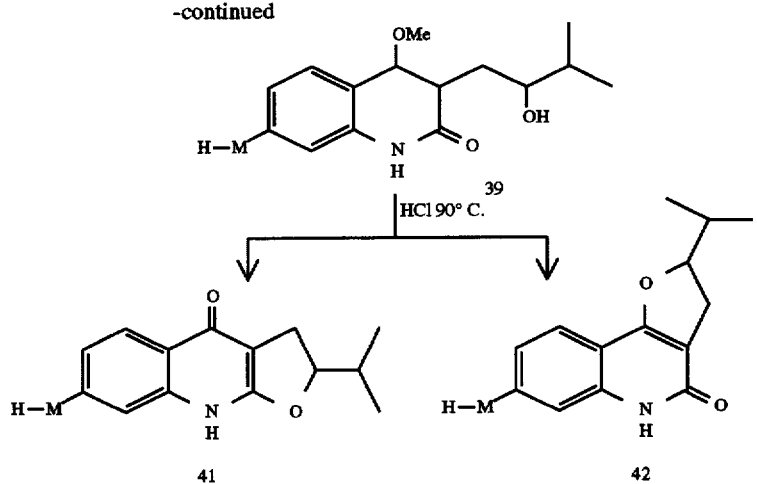

Formula (XX):

A commercially available substituted phenol, i.e., orcinol, olivetol, ect., can be used as a starting material for the compounds according to formula (XX), according to known method steps.

One particularly useful compound, identified here as XL-3-44 (compound 3Ca), can be prepared as shown in Scheme 2A Scheme 2A

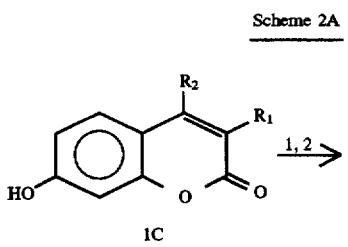

a $R_1 = H, R_2 = CH_3$
b $R_1 = Cl, R_2 = CH_3$

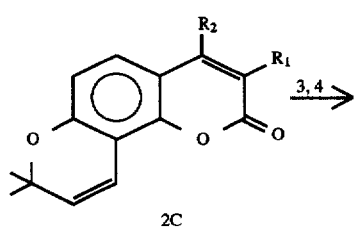

-continued
Scheme 2A

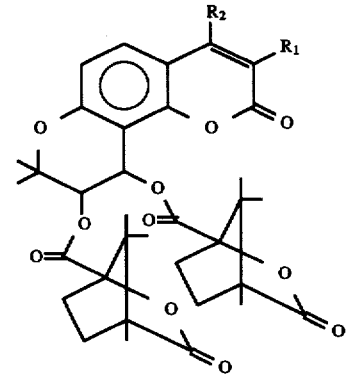

3C
a $R_1 = H, R_2 = CH_3$ (XL-3-44)
b $R_1 = Cl, R_2 = CH_3$ (XL-3-45)

(1) A mixture of 5 mmol of the 7-hydroxycoumarin derivative compound, 1Ca and 1Cb, 12.5 mmol of potassium carbonate, 2.5 mmol potassium iodide, and excess 2-methyl-2-chloro-3-butyne in 50 mL dimethyl formamide (DMF) was stirred and heated at 60° C. for 2-3 days. The potassium carbonate was filtered out, and the reaction mixture was concentrated in vacuo. The residue was poured into ice water and left overnight. The off-white solid product was collected by filtration. The yield was 34-50%.

(2) The product of step (1) in N,N-diethylaniline was heated to boiling for eight hours. After a general conventional work-up procedure, the yield of compound 2C was 60-75%.

(3) A mixture of 0.005 mmol of $(DHQ)_2$-PYR, 0.75 mmol $K_3Fe(CN)_6$, 0.75 mmol $K_2CO_3$, 0.005 mmol of $K_2OsO_2(OH)_4$, 2.5 mL t-butyl alcohol/water, 1:1 v/v, and 0.25 mmol compound 2C was stirred at 0° C. for 3-5 days. Then, $NaS_2O_5$, water and chloroform were added to the mixture, which was stirred at room temperature for 0.5 hour. The organic phase was separated, and the water phase was extracted three times with $CHCl_3$. The organic phases were combined and the solvent was removed in vacuo. The residue was the desired diol product.

(4) After the crude diol was dried, it was reacted directly with excess (−)-(S)-camphanoyl chloride in pyridine and methylene chloride at room temperature for 48 hours. After a general conventional work-up procedure, the diester product 3Ca, was obtained and was purified by TLC using hexane/ethyl acetate 3:1. The yield was 50% The structure of 3Ca was determined by $^1$H-NMR, MS, IR and elemental analyses. The enantiomeric excess was determined by $^1$H-NMR analysis of the bis(−)-camphanic esters.

Testing HIV activity in vitro

The following are examples of methods which can be used to screen suksdorfin analogs according to Formula G-1, G-2, and/or one or more of (I)–(XX), for determining at least one therapeutic utility and/or mechanism of action as an anti-viral compound, such as anti-HIV compound; without undue experimentation, based on the teaching and guidance presented herein.

First various concentrations of suksdorfin analogs can be incubated with a chronically HIV-1 infected T cell line, e.g., ACH-2, and a chronically HIV-1 infected monocytic cell line, e.g., U1. These cell lines are useful in predicting if suksdorfin analogs of the present invention could induce virus expression in vivo when given to an individual who is latently infected with HIV and not actively expressing virus. In addition, when these two cell lines are incubated with the phorbol ester, PMA, HIV-1 expression is increased. Since suksdorfin analogs of the present invention can inhibit virus replication during an acute HIV-1 infection of H9 cells, it will be of interest to determine if it can also suppress HIV-1 expression from these two chronically infected cell lines when they are stimulated with PMA.

Suksdorfin analogs of the present invention can be tested with other cell types (e.g., freshly isolated cells and/or cell lines) which are infected with HIV. Freshly isolated monocyte/macrophages and peripheral blood mononuclear cells (PBMCs) can be infected with a monotropic isolate of HIV-1, Ba-L and/or a laboratory isolate (e.g., IIIB) of HIV-1, respectively. In addition, virus suppression can be evaluated when a suksdorfin analog is added to acutely HIV-1 (IIIB isolate) infected monocytic cell line, U937, and/or the HIV-2 (D194 isolate) infected T cell line, HUT-78. These studies will determine if the suppressive effect of various suksdorfin analogs are specific to a particular cell phenotype or a virus isolate.

Other studies can also be used to screen for the mechanism of action (MOA) of suksdorfin analogs according to at least one of formula (G-1), (G-2), and (I)–(XX), e.g., by:

(a) determining if the compound is capable of inactivating HIV-1 by culturing suksdorfin with HIV-1 for 1 hour before adding the virus to H9 cells;

(b) determining if the compounds' MOA is by competing with HIV for the same receptor (CD4) on the cell surface. This can be tested by adding HIV-1, suksdorfin analogs and H9 cells together and then monitoring the amount of virus produced in the presence and absence of suksdorfin analogs;

(c) H9 cells will also be pretreated with suksdorfin analogs to determine if the effect of the drug is on the cells or on the virus.

(d) Molecular biology studies, wherein DNA and/or RNA levels can be measured in cells that had been treated with various concentrations of suksdorfin. This will be preferred where negative results are obtained from one or more of methods (a)–(c). Both cellular and/or viral regulatory elements can be examined.

Suksdorfin analogs can also be tested in the presence of nucleoside analogs (AZT, ddI, ddC) or other accepted anti-HiV agents, to determine if suksdorfin analogs are synergistic with any of these currently licensed anti-retroviral agents which can ultimately enhance their individual suppressive capability especially at lower concentrations.

A suksdorfin analog of the present invention can be used for treatment of retroviral (e.g., HIV) infection either alone, or in combination with other modes of therapy known in the art. Such modes of therapy can include chemotherapy with drugs, such as, but not limited to, at least one of AZT, ddC, ddA, ddT, ddI, or any other anti-retroviral antibodies in combination with each other, or associated with a biologically based therapeutic, such as, for example, soluble CD4, antibodies to CD4, and conjugates of CD4 or anti-CD4, or as additionally presented herein.

Because suksdorfin analogs of the present invention are relatively less or substantially non-toxic to normal cells, their utility is not limited to the treatment of established retroviral infections. For example, a suksdorfin analog according to formulae (I) to (XX) can be used in the treatment of blood products, such as those maintained in blood banks. The nation's blood supply is currently tested for antibodies to HIV. However, the test is still imperfect and samples which yield negative tests can still contain HIV virus. Treating blood and blood products with the proteins and derivatives of the present invention can add an extra margin of safety, to kill any retrovirus that can have gone undetected.

Pharmaceutical Compositions

Pharmaceutical compositions of the present invention can comprise at least one suksdorfin analog according to at least one of formulae (I), (II), (G-1), (G-2), and (III)–(XX). Pharmaceutical compositions according to the present invention can also further comprise other anti-viral agents, such as, but not limited to, AZT, ddI, 2'-β-fluoro-ddI, ddA, ddG, ddC, 2'-β-fluoro-ddC , d4T, AzddU, phosphonylmethoxyethyl-adenine, or soluble CD4, or immunomodulators, e.g., as presented below. For a review of therapeutic agents in HIV infection, see, e.g., Mitsuya, H. et al., *FASEB J.* 5:2369–2381 (1991), which reference is hereby incorporated by reference.

Additional suitable antiviral agents for optimal use with a coumarin compound of the present invention can include, but are not limited to, AL-721 (lipid mixture) manufactured by Ethigen Corporation and Matrix Research Laboratories; Amphotericin B methyl ester; Ampligen (mismatched RNA) developed by DuPont/HEM Research; anti-AIDS antibody (Nisshon Food); AS-101 (heavy metal based immunostimulant); AZT (azidothymidine/Retrovir/Zidovudine) manufactured by Burroughs Wellcome; Betaseron (β-interferon) manufactured by Triton Biosciences (Shell Oil); butylated hydroxytoluene; Carrosyn (polymannoacetate) Castanospermine; Contracan (stearic acid derivative); Creme Pharmatex (contains benzalkonium chloride) manufactured by Pharmelac; CS-87 (5-unsubstituted derivative of Zidovudine); Cytovene (ganciclovir) manufactured by Syntex Corporation; DDC (dideoxycytidine) manufactured by Hoffann-La Roche and other nucleoside analogues; dextran sulphate; D-penicillamine (3-mercapto-D-valine) manufactured by Carter-Wallis and Degussa Pharmaceutical; Foscarnet (trisodium phosphonoformate) manufactured by Astra AB; fusidic acid manufactured by Leo Lovens; glycyrrhizin (a constituent of liquorice root): HPA-23 (ammonium-21-tungsto-9-antimonate) manufactured by Rhone-Poulenc Sante; human immunevirus antiviral developed by Porton Products International; Ornidyl (eflornithine) manufactured by Merrell-Dow; Nonoxinol; pentamidine isethionate (PENTAM-300) manufactured by Lypho Med; Peptide T (octapeptide sequence) manufactured by Peninsula Laboratories; Phenytoin (Warner-Lambert); Ribavirin; Rifabutin (ansamycin) manufactured by Adria Laboratories; rsT4 (recombinant soluble T4) manufactured by Biogen, Genentech and Smith Kline & French; Trimetrexate manufactured by Warner-Lambert Company; SK-818 (germanium-derived antiviral) manufactured by Sanwa Kagaku; suramin and analogues thereof manufactured by Miles Pharmaceuticals; UA001 manufactured by Ueno Fine Chemicals Industry; Wellferon (α-interferon) manufactured by Burroughs Wellcome; Zovirex (acyclovir, AZT) manufactured by Burroughs Wellcome.

Pharmaceutical compositions of the present invention can also further comprise immunomodulators. Suitable immunomodulators for optional use with a coumarin compound of the present invention in accordance with the invention can include, but are not limited to: ABPP (Bropirimine): Ampligen (mismatched RNA) (DuPont/HEM Research); anti-human interferon-αantibody (Advance Biotherapy and Concepts); anti-AIDS antibody (Nisshon Food): AS-101 (heavy metal based immunostimulant), ascorbic acid and derivatives thereof; interferon-β; Carrosyn (polymannoacetate); Ciamexon (Boehringer-Mannheim); Cyclosporin; Cimetidine; CL-246,738 (American Cyanamid); colony stimulating factors, including GM-CSF (Sandoz; Genetics Institute; dinitrochlorobenzene; interferonα; interferon-gamma; glucan; hyperimmune gammaglobulin (BAYER); IMREG-1 (leucocyte dialyzate) and IMREG-2 (IMREG Corp.); immuthiol (sodium diethylthiocarbarmate) (Institut Merieux); interleukin-1 or interleukin-2 (Cetus Corporation; Hoffman-La Roche; Immunex); isoprinosine (inosine pranobex); Krestin (Sankyo); LC-9018 (Yakult); lentiLart (Ajinomoto/Yamanouchi); LF-1695 (Fournier); methionine-enkephalin (TNI Pharmaceuticals; Sigma Chemicals); Minophagen C; muramyl tripepride, MTP-PE (Ciba-Geigy); naltrexone ("Trexan" (DuPont); Neutropin; RNA immunomodulator (Nippon Shingaku); shosaikoto and ginseng; thymic humoral factor; TP-5 (Thymopentin) (Ortho Pharmaceuticals; Thymosin fraction 5 and Thymosin 1; Thymostimulin; TNF (tumor necrosis factor) manufactured by Genentech; and vitamin B preparations.

The preferred animal subject of the present invention is a mammal. By the term "mammal" is meant an individual belonging to the class Mammalia. The invention is particularly useful in the treatment of human subjects.

By the term "treating" is intended the administering to subjects of a suksdorfin analog or derivative for purposes which can include prevention, amelioration, or cure of a retroviral-related pathology.

Medicaments are considered to be provided "in combination" with one another if they are provided to the patient concurrently or if the time between the administration of each medicament is such as to permit an overlap of biological activity.

In one preferred embodiment, at least one suksdorfin analog comprises a single pharmaceutical composition.

Pharmaceutical compositions for administration or diagnosis of the present invention can comprise at least one suksdorfin analog according to at least one of Formulae (G-1), (I) and/or (II) in pharmaceutically acceptable form optionally combined with a pharmaceutically acceptable carrier. Such compositions can be administered by any means that achieve their intended purpose. Amounts and regimens for the administration of a suksdorfin analog of the present invention can be determined readily by those with ordinary skill in the clinical art of treating a retroviral related pathology.

For example, administration can be by parenteral, such as subcutaneous, intravenous, intramuscular, intraperitoneal, transdermal, or buccal routes. Alternatively, or concurrently, administration can be by the oral route. The dosage administered will be dependent upon the age, health, and weight of the recipient, kind of concurrent treatment, if any, frequency of treatment, and the nature of the effect desired.

Compositions within the scope of this invention include all compositions wherein at least one suksdorfin analog according to formula (I), (II) or (G-1) is comprised in an amount effective to achieve its intended purpose. While individual needs vary, determination of optimal ranges of effective amounts of each component is within the skill of the art. Typical dosages comprise 0.1 to 100 mg/kg/body weight. The preferred dosages comprise 1 to 100 mg/kg/body weight. The most preferred dosages comprise 10 to 100 mg/kg/body weight.

Therapeutic administration can also include prior, concurrent, subsequent or adjunctive administration of at least one additional sukdorfin or other therapeutic agent, as an anti-viral or immune stimulating agent. In such an approach, the dosage of the second drug can preferably be the same or different that as the dosage of the first therapeutic agent. Preferably, the drugs are administered on alternate days in the recommended amounts of each drug.

Administration of a compound of the present invention can also optionally include previous, concurrent, subsequent or adjunctive therapy using immune system boosters or immunomodulators. In addition to the pharmacologically active compounds, a pharmaceutical composition of the present invention can also contain suitable pharmaceutically acceptable carriers comprising excipients and auxiliaries which facilitate processing of the active compounds into preparations which can be used pharmaceutically. Preferably, the preparations, particularly those preparations which can be administered orally and which can be used for the preferred type of administration, such as tablets, dragees, and capsules, and also preparations which can be administered rectally, such as suppositories, as well as suitable solutions for administration by injection or orally, contain from about 0.01 to 99 percent, preferably from about 20 to 75 percent of active compound(s), together with the excipient.

Pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, e.g., fillers such as saccharide, for example, lactose or sucrose, mannitol or sorbitol, cellulose preparations and/or calciumphosphates, for example, tricalcium phosphate or calciumhydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents can be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions can be used, which can optionally contain gum arabic, talc, polyvinyl pyrrolidone, polyethylene glycol and/or titaniumdioxide, lacquer solutions and suitable organic solvents or solvent mixtures. In order to produce coatings resistant to gastric juices, solutions of suitable cellulose preparations such as acetylcellulose phthalate or hydroxypropymethyl-cellulose phthalate are used. Dye stuffs or pigments can be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which can be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils or liquid paraffin. In addition, stabilizers can be added.

Possible pharmaceutical preparations which can be used rectally include, for example, suppositories which consist of a combination of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts. In addition, suspensions of the active compounds as appropriate oily injection suspensions can be administered. Suitable lipophilic solvents or vehicles include fatty oils, for example, sesame oil, or synthetic fatty acid esters, for example, ethyl oleate or triglycerides. Aqueous injection suspensions that can contain substances which increase the viscosity of the suspension include, for example, sodium carboxymethyl cellulose, sorbitol, and/or dextran. Optionally, the suspension can also contain stabilizers.

A pharmaceutical formulation for systemic administration according to the invention can be formulated for enteral, parenteral or topical administration. Indeed, all three types of formulation can be used simultaneously to achieve systemic administration of the active ingredient.

Suitable formulations for oral administration include hard or soft gelatin capsules, dragees, pills tablets, including coated tablets, elixirs, suspensions, syrups or inhalations and controlled release forms thereof.

Solid dosage forms in addition to those formulated for oral administration include rectal suppositories At least one suksdorfin analog can also be administered in the form of an implant.

Suitable formulations for topical administration include creams, gels, jellies, mucilages, pastes and ointments. The compounds can also be formulated for transdermal administration, for example, in the form of transdermal patches so as to achieve systemic administration.

Suitable injectable solutions include intravenous subcutaneous and intramuscular injectable solutions. At least one suksdorfin analog can also be administered in the form of an infusion solution or as a nasal inhalation or spray.

Having now generally described the invention, the same will be more readily understood through reference to the following examples which are provided by way of illustration, and are not intended to be limiting of the present invention, unless specified.

EXAMPLE I

Isolation and Purification of Suksdorfin Analog of the Present Invention

Suksdorfin was obtained as colorless needles (m.p. 140°–141° C.) by silica gel chromatography of the active hexane fractions. Its molecular formula was determined to be $C_{21}H_{24}O_7$ by high resolution mass spectroscopy, and a comparison of the UIL, IR, and $^1$H-NMR spectral data with those described in the literature identified 1 as suksdorfin, which had been previously isolated from this same plant by Willette and Soine (Willette, R. E.; Soine, T. O. J. Pharm. Sci., 1962, 51, 149).

Suksdorfin demonstrated potent inhibitory activity against HIV-1 replication in acutely infected H9 cells with an $EC_{50}$ of 1.3 µM as determined by a p24 antigen ELISA assay and it inhibited uninfected H9 cell growth with an $IC_{50}$ of >52 µM (Table 1). The therapeutic index ($IC_{50}$ for cell growth inhibition divided by $EC_{50}$ for HIV inhibition) for suksdorfin compound 1 was >40. In comparison, the therapeutic index of dideoxyinasins (ddI), a dideoxynucleaside which inhibits reverse transcriptase, when tested in our assay system was only 10-fold greater (>400) than that observed with suksdorfin.

In order to elucidate structure-activity relationships, the HIV-replication inhibitory effects of ten coumarins, which are isolated from various plant sources (Soine, T.; O. J. Pharm. Sci., 1964, 53, 231), was determined and compared with that of 1. The compounds include an additional dihydroseselin type angular pyranocoumarin, 2 (pteryxin), a dihydro-angelicin type angular coumarin, 3 (columbianadin), three dihydroangelicin linear furanocourins, 4 (nodakenetin), 5 (nodakenin), and 6 (acetylnodakenin), four psoralen type linear furanocoumarins, 7 (imperatorin), 8 (bergapten), 9 (isoimperatorin), and 10 (oxypeucedanin), and a dicoumaryl ether, 11 (daphnoretin).

As shown in Table 1, only 1 showed potent anti-HIV-1 activity at nontoxic concentrations. All other compounds (2–11) were either inactive or were less active and more toxic. The 4'-isovaleryl group of 1 was important for selective HIV-1 inhibition. Replacement of this group with an angeloyl moiety as in pteryxin (2) in-creased the toxicity by 5-fold and slightly reduced anti-HIV-1 activity. The furanocoumarins (3–10) were inactive or active only at toxic concentrations, (e.g., the therapeutic index of 3 was >1.3). The dicoumaryl ether (11) showed no activity.

TABLE 1

HIV Inhbitions[5] by Suksdorfin (1) and Related Compounds (2-11).

| Compound | IC$_{50}$ (µM)[a] | EC$_{50}$ (µM)[b] | Therapeutic Index |
|---|---|---|---|
| 1 Suksdorfin | >52 | 1.3 | >40 |
| 2 Ptyeryxin | >10.4 | 4.6 | >3.7 |
| 3 Columbianadin | >6.1 | 4.6 | >1.3 |
| 4 Nodakenetin | ND[c] | Inactive[d] | ND |
| 5 Nodakenin | ND | Inactive | ND |
| 6 Acetylnodakenin | ND | Inactive | ND |
| 7 Imperatorin | >74.1 | 11.1 | >6.7 |
| 8 Bergapten | >92.6 | 30.1 | >3.1 |
| 9 Isoimperatorin | >185.2 | 40.7 | >4.6 |
| 10 Oxypeucedanin | >69.9 | 31.5 | >2.2 |
| 11 Daphnoretin | ND | Inactive | ND |

When compound XL-3-44 was tested for HIV inhibition in the manner described above, the IC$_{50}$ (µg/ml) was >100, and further delutions must be made to obtain EC$_{50}$ (µg/ml) and Therapeutic Index Values.
[a]Concentration which inhibits uninfected cell growth by 50%
[b]Concentration which inhibits viral replication by 50%
[c]ND - not determined
[d]No suppression of HIV-1 replication in H9 cells

EXAMPLE II

In Vitro HIV Inhibition Activity Assays

H I V inhibition assay. The HIV inhibition was measured as described herein. Briefly, H9 cells, a T cell line, (3.5×10$^6$ cells/ml) were incubated in the presence or absence of HIV-1 (IIIB strain, 0.01–0.1 TCID$_{50}$/cell) for 1 hour at 37° C. Cells were washed thoroughly and resuspended at a final concentration of 2×10$^5$ cells/ml in the presence or absence of compound. After incubation for 3–4 days at 37° C., the cell density of uninfected cultures was determined by cell count to assess toxicity of the drug. An aliquot of each cell-free supernatant was assayed by p24 antigen ELISA to quantitate the amount of HIV-1 present in the infected cultures. Test compounds were considered to be active at a particular concentration if p24 antigen levels were less than 70% of infected, untreated controls and were nontoxic to uninfected H9 cells.

EXAMPLE III

Synthesis of Suksdorfin Analogs

Synthesis of Seselin (2) (Scheme 1)

The construction of the pyran ring from commercially available 7-hydroxycoumarin (1) involved two steps, which have been described by Hlubucek, et al. *Aust. J. Chem.* 24:2347 (1971). The crude product of the first step was used directly in the next rearrangement reaction, which produced seselin (2) in good yield. Seselin was then used as the starting material for the synthesis of other pyranocoumarin derivatives as described below. (±)-3',4'-Di-0-acyl-cis-khellactone derivatives (Scheme 1). The 3',4'-di-0-acyl-cis-khellactone derivative compounds 12–21 can be prepared by two routes. In the first, seselin (compound 2) was functionalized at the 3',4' positions by oxidation with m-chloroperoxybenzoic acid to give the (±)-3'-hydroxy-4'-0-acyl derivative compound 3 (Schroeder et al, *Chem. Ber.* 92, 2388, (1959)). Tosic acid catalyzed dehydration transformed compound 3 to an optically inactive 3-keto derivative compound 4 (Willette et al *J. Pharm. Sci.* 51, 149 (1962)). According to a literature method (S. N. Shanbhag et al *Tetrahedron*, 21:3591 (1965)), treatment of compound 4 with lead tetraacetate in acetic acid should yield the racemic compound 5, despite the low yield reported in this transformation. After saponification and reesterification at C-4' to give a 3'keto-4'-0-acyl intermediate compound 6, the ketone can be reduced to a hydroxyl group with NaBH$_4$ (Shanbhag, supra). Further esterification of this (±)-mono ester khellactone with RCOCl or (RCO)$_2$O could furnish the desired (±)-di-0-acyl-khellactone derivatives, followed by careful chromatographic separation of their cis racemic mixture.

In the second route, seselin compound 2 was oxidized with OsO$_4$ to give the cis-khellactone intermediate compound 7 in good yield (Schroeder et al, supra). The 3',4'-di-0-ester-cis-khellactone derivative compounds 12–17, in which the two ester groups at 3' and 4' are identical, were produced using standard esterification conditions. However, by using equal molar reagents and mild reaction conditions, selective esterification could be achieved giving the 3'-mono compounds 8,9* and 4'-mono ester khellactone compounds 10,11*, in a mixture with the diesters. Separation and further esterification of these mono ester compounds 8–11* using acetic anhydride yielded the desired (±)-3',4'-di-0-acyl-cis-khellactone derivative compounds 18–21*, which have different ester moieties at the 3' and 4' positions. This method has fewer steps and gives better yields than the previous route through compound 4. However, OsO$_4$ is very toxic and expensive, which limits its extensive use. (±)-3'-O-acyl-jatamansinol derivatives (Scheme 2)

Jatamansinol derivatives were synthesized using a literature method (Murry et al *Tetrahedron letters* 27:4901 (1971)). A phenyl group was introduced at C-8 of 7-hydroxycoumarin (1) in a three-step sequence, which involved a Claisen rearrangement. Under slightly acidic conditions, cyclization of intermediate compound 23 furnished jatamansinol compound 24. Using standard esterification conditions, (±)-3'-0-acyl-jatamansinol derivatives (compounds 25, 26) were synthesized, as shown in Scheme 3. (±)-3',4'-Di-0-acyl-trans-khellactone derivatives and 3'-0-alkyl-4'-0-acyl-trans-khellactone derivatives (Scheme 4)

Preparation of the 3',4'-trans derivatives proceeds from intermediate compound 3. Compound 3 was esterified by treatment with the appropriate acyl chloride or acid anhydride to produce the 3',4'-di-0-acyl-trans-khellactones (compounds 27,28,33,34). Reaction of compound 3 with various alkylating reagents (MeI, benzyl bromide, dihydropyran) gave the 3'-alkyl intermediate compounds 29–32. Saponification of these compounds gave the 3'-alkyl-4'-hydroxy derivative compounds 35–38. After esterification with an acyl chloride or acid anhydride, the (±)-3'-O-alkyl-4'-O-acyl-trans-khellactone derivative compounds 39–42 were synthesized.

(±)-Benzodihydropyran derivatives (Scheme 4)

The lactone ring in compound 3 or in the 3',4'-diacyl-trans derivatives was abolished using a basic hydrolysis procedure to give new (±)-benzodihydropyran compound 43. The base (KOH, Ag$_2$O, or NaH) cleaves the lactone ring and the ester groups. The free acid or the hydroxyl groups can then undergo alkylation by MeI.

Optically pure ester derivatives (compounds 8–11*, 14–21*, 33, 34*) were obtained using an optically active acyl chloride or acid anhydride. The products are diastereoisomers, which can be separated with repeated chromatography.

EXAMPLE II

Anti-HIV Activity of Suksdorfin Analogs against HIV-infected H9 lymphocytes

The inhibitory activities of the synthesized suksdorfin analogs against HIV-replication in H9 lymphocytes were examined. The compounds include cis-(compounds 8–15) and trans-(compounds 27–32) khellactone derivatives, jatamansinol derivatives (compounds 25–26), and optically pure cis-(compounds 16–17) and trans-(compounds 44–45) khellactone derivatives.

As shown in Table 3, compound 16 exhibited potent anti-HIV activity. The $ED^{50}$ value of compound 16 is at least 0.00041 µM and its therapeutic index is over 78,125 but less than 390,625. This activity is much better than that of suksdorfin. Since the $ED_{50}$ value and therapeutic index of AZT in this assay system are 0.04 µM and 50,000, respectively, the anti-HIV activity of compound 16 is more potent than that of AZT.

The diastereomer of compounds 16(17), as well as compounds 44 and 45, which are trans-khellactone derivatives with same acyl groups, showed much less activity than that of compound 16.

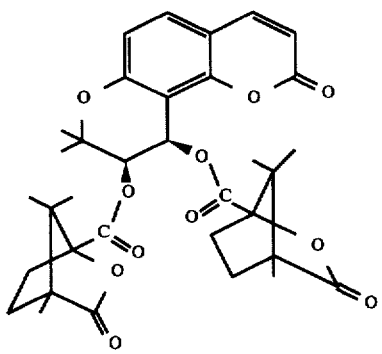
(16)

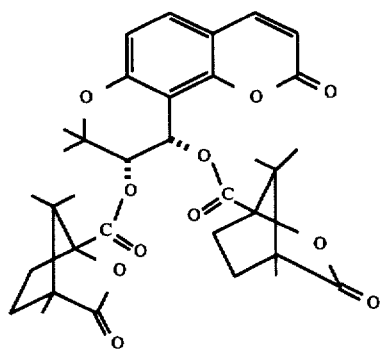
(17)

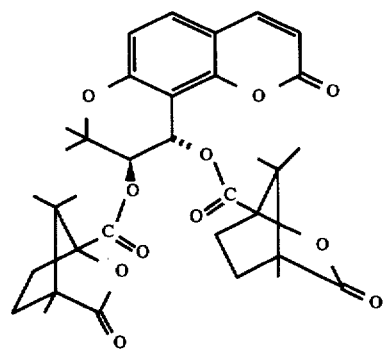
(44)

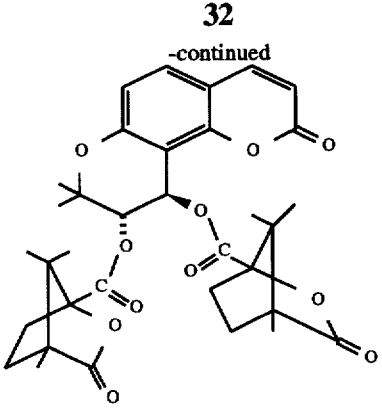
(45)

TABLE 3

HIV Inhibition by Synthesized Suksdorfin Derivatives

| Compound | $IC_{50}$ (µM) | $EC_{50}$ (µM) | Therapeutic Index |
|---|---|---|---|
| 8 and 9 | ND | >57.8 | ND |
| 10 and 11 | ND | >57.8 | ND |
| 12 | ND | >289 | ND |
| 13 | ND | >232 | ND |
| 14 and 15 | >47 but <233 | 7.0 | >6.7 but <33.3 |
| 25 | ND | >69 | ND |
| 26 | ND | >12 | ND |
| 27 | ND | >45 | ND |
| 28 | 10 | 8.3 | 1.2 |
| 29 | >48 | 241 | >0.2 |
| 30 | >8 but <41 | 6.1 | >1.3 but <6.7 |
| 31 | ND | >41 | ND |
| 32 | >40 but <200 | 8.3 | >5 but <25 |
| 16 | >32 but <160 | 0.00041 | >78,125 but <390,625 |
| 17 | 1,700 | 51 | >33.3 |
| 44 | >6.4 and <32 | >6.4 but <32 | >1 |
| 45 | <32 | 32 | >1 |
| AZT | 2000 | 0.04 | 50,000 |

EXAMPLE II

Activity of Suksdorfin Against HIV-Infected ACH-2 and U1 Cells

Effects of suksdorfin analogs on Chronically HIV-1 infected cells. The experimental design is as follows: The phorbol ester, PMA ($10^{-8}$M) and various concentrations of suksdorfin were either added or not added to both the chronically HIV-1 infected T cell line (ACH-2) and to the chronically HIV-1 infected monocytic cell line (U1). Cell-free supernatant was collected 72 hours post culture for p24 antigen ELISA.

The chronically HIV-1 infected cell lines, ACH-2 and U1 have been used extensively in the literature. When either cell line is cultured with PMA or various cytokines the level of HIV-1 expression as determined by p24 antigen ELISA is increased. Since suksdorfin suppressed virus replication in acutely HIV-1 infected H9 cells, it was important to determine if it would have an effect on chronically HIV-1 infected cells. In addition, these two cell lines are helpful in predicting whether a drug might increase the in vivo replication of HIV in an individual who is latently virallyoinfected.

Therefore, the questions which this experiment addressed were the following:

1. Does suksdorfin cause an increase in the amount of virus replication from either chronically T or monocyte/ macrophage infected cell line. The answer is no. This information is important to the FDA, since they will not permit administering an agent in vivo to an individual that might cause an increase in virus replication.

2. Does suksdorfin alter the amount of virus replication from PMA-stimulated chronically HIV-1 infected cells? The answer is no. There was no significant alteration in the level of virus expression as measured by p24 antigen ELISA when PMA was added to cells which were also cultured in the presence of suksdorfin. Suksdorfin did not increase the amount of virus produced by PMA alone. The above determinations were based in part on the data presented in Table 4.

TABLE 4

| Suksdorfin Concentration | ACH-2 Cells | | U1 Cells | |
|---|---|---|---|---|
| | −PMA | +PMA | −PMA | +PMA |
| 0 μg/ml | 3,676 pg/ml | 52,122 pg/ml | 0 pg/ml | 6,963 pg/ml |
| 20 μg/ml | 4,541 pg/ml | 49,914 pg/ml | 0 pg/ml | 5,096 pg/ml |
| 4 μg/ml | 4,723 pg/ml | 61,235 pg/ml | 0 pg/ml | 9,728 pg/ml |
| 0.8 μg/ml | 3,821 pg/ml | 55,910 pg/ml | 0 pg/ml | 7,360 pg/ml |
| 0.16 μg/ml | 3,688 pg/ml | 50,775 pg/ml | 0 pg/ml | 6,611 pg/ml |

There was a higher background in the ACH-2 cells (3,676 pg/ml) than compared to the U1 cells (0 pg/ml). A known vital inducer, when added to each cell line, caused a significant increase in the amount of p24 antigen in those cultures.

EXAMPLE III

Combination Study of Suksdorfin with AZT, ddI and ddC

The data presented in Table 5 show toxicity data on a suksdorfin. The $IC_{50}$ value has decreased from >20 but <100 to >4 but <20 and the $EC_{50}$ value has increased from 0.5–0.8 to 1.5–2.8 μg/ml.

Suksdorfin is found to act synergistically with AZT, ddI ddC. The 20 μg/ml concentration of suksdorfin was toxic H9 cells. The 4 μg/ml concentration of suksdorfin inhibited HIV-1 replication by 64% but when it was added to HIV-1 infected cultures containing AZT (0.0001 μg/ml) the $EC_{50}$ concentration decreased by 400-fold and the TI value increased 400-fold. Likewise, 4000-fold less ddI was needed when 4 μg/ml of suksdorfin was present in the cultures as when ddI was used alone. Forty-fold less ddC was needed when it was added to cultures containing 4 μg/ml of suksdorfin. This is significant data demonstrating that suksdorfin is expected to be useful in increasing the anti-HIV activity and/or decreasing the toxicity of these other FDA-approved drugs.

TABLE 5

| Compound | Purity | $IC_{50}$ (μg/ml) | $EC_{50}$ (μg/ml) | Therapeutic Index |
|---|---|---|---|---|
| Suksdorfin | pure | >4 but <20 | 2.8 | >1.4 but <7.1 |
| AZT | pure | >1 | 0.04 | >25 |
| ddI | pure | >1 | 0.4 | >2.5 |
| ddC | pure | >1 | 0.004 | >250 |
| 4 μg/ml Suksdorfin + AZT | pure | >1 | <0.0001 | >10,000 |
| μg/ml Suksdorfin + | pure | >1 | <0.0001 | >10,000 |

TABLE 5-continued

| Compound | Purity | $IC_{50}$ (μg/ml) | $EC_{50}$ (μg/ml) | Therapeutic Index |
|---|---|---|---|---|
| ddI μg/ml Suksdorfin + ddC | pure | >1 | <0.0001 | >10,000 |

EXAMPLE IV

Anti-HIV Activity of Suksdorfin

Suksdorfin was tested on peripheral blood mononuclear cells (PBMCs) which were stimulated for 3 days with PHA (1 μg/ml). The cells were collected and then infected with the 20X stock HIV-1 (IIIB). This is the same virus that is used in the drug screening assay. PBMCs were used for the following reasons: (1) It is another type of T cell infection. (2) PMBCs are freshly isolated cells not a cell line as are H9 cells. (3) We need to know if the effects of suksdorfin were limited to only an acute HIV-1 infection of a T cell line such as H9 cells. After the cells were infected with HIV-1, the cells were washed and then placed in medium with the cytokine, interleukin 2 (IL-2). IL-2 is needed to keep the cells activated which is necessary also for virus replication.

Suksdorfin was also tested on an acute HIV-1 infection of the promonocytic cell line, U937. This was done again to determine drug specificity but this time on a monocytic cell line.

As the data indicates, suksdorfin can suppress an acute HIV-1 replication in fresh PBMCs (a T cell infection) and in U937 cells (a monocytic cell line). The data from the PBMC infection correlates with other data in which H9 cells (a T cell line) were infected with HIV-1 and then suksdorfin was added. The $EC_{50}$ was 1.5, as presented in Table 6. The $EC_{50}$ value determined from the U937 cells was approximately one third of that for the PBMCs.

TABLE 6

| Compound | Purity | $IC_{50}$ (μg/ml) | $EC_{50}$ (μg/ml) | Therapeutic Index |
|---|---|---|---|---|
| Suksdorfin + PBMCs | pure | >4 but <20 | 1.5 | >2.7 but <13.3 |
| U937 cell line | | >20 | 0.58 | >34.5 |

EXAMPLE V

Anti-HIV Activity Results for Suksdorfin Analog Compounds

Table 7 shows results from 4 separate assays as presented in the above examples on compound 16 when tested alone and data from 1 experiment when tested in combination with either AZT, ddI, or ddC.

Compound 16 was tested for its ability to inhibit HIV-1 replication in H9 cells. An activity was found of 256 pg/ml (0.0041 μM). The $IC_{50}$ range (>32 but <160) was consistent and showed low toxicity. $EC_{50}$ results: 3 assays demonstrated significant suppression. During the assays the agent mediated 44% and 35% suppression at 0.000256 μg/ml, respectively. The $EC_{50}$ value was at least about 0.000256 μg/ml (256 pg/ml [0.00041 μM]. Based on an $EC_{50}$ value of 256 pg/ml, the TI was >78,125 but <390,625 for 16 (LH70C1-4L).

TABLE 7

| 16 (LH70C1-4L) | Purity | $IC_{50}$ (µg/ml) [µM] | $EC_5$ (µg/ml) [µM] | Therapeutic Index |
|---|---|---|---|---|
| | pure | >20 but <100 (>32 but <160) | 0.000256 (0.00041) | >78,125 but >390,625 |

Results from Chronic U1 Experiment with 16

Compound 16 was also assayed on ACH-2 (chronically HIV-1 infected T cell line). U1 cells are also chronically HIV-1 infected cells but they are from the monocytic cell line, U937. The data presented in Table 8 indicates the following points:

Compound 16 (without PMA) did not induce the U1 cells to make virus. This was also the same for AZT. The amount of HIV-1 present in these supernatants is very low and not significantly above assay background. The fact that the drug did not induce virus replication is important since individuals tend to be latently infected with HIV; therefore, it is important that a drug not increase in vivo viral burden during therapy, as shown by this data.

Compound 16 (with PMA) did not suppress virus replication. The results were identical to AZT. This is not surprising since AZT does not have an effect on chronically HIV infected cells (in the literature) since reverse transcription has already occurred.

There was good virus expression in the control U1 sample as compared to background. The various drug-treated samples were not significantly different than control. For there to be a significant increase, the amount of p24 antigen in the supernatant needs to increase at least 4–5 fold. This was not the case.

Results of testing the ability of compound 16 to suppress virus replication during an HIV-2 infection of HUT-78 cells.

During this experiment, HIV-2 was used. The basic assay system is identical to that used for HIV-1 except that a different virus stock was used and rather than a p24 antigen ELISA determination a reverse transcriptase assay was used to detect the presence of the virus.

As the data indicates in Table 9, compound 16 had no effect on the virus replication of HIV-2. This data will help in designing future experiments especially as they relate to animal model system for testing the in vivo activity of compound 16. Compound 16 will also be tested in simian immunodeficiency virus (SII)-infected cells since SII and HIV are similar.

AZT was used as a positive drug control and it inhibited HIV-2 replication.

TABLE 8

| Sample Identification | P24 pg/ml | |
|---|---|---|
| | –PMA | +PMA |
| U1 control | 0 | 5660 |
| U1 + LH70C1-4L 16 [µM] | | |
| (20 µg/ml) [32] | 95 | 9530 |
| (4 µg/ml) [6.4] | 41 | 8742 |
| (0.8 µg/ml) [1.3] | 88 | 8390 |

TABLE 8-continued

| Sample Identification | P24 pg/ml | |
|---|---|---|
| | –PMA | +PMA |
| (0.16 µg/ml) [0.26] | 76 | 7162 |
| (0.032 µg/ml) [0.051] | 101 | 8090 |
| (0.0064 µg/ml) [0.010] | 90 | 6419 |
| (0.00128 µg/ml) [0.0021] | 99 | 6335 |
| (0.00025 µg/ml) [0.00040] | 78 | 7757 |
| (0.0000512 µg/ml) [0.000084] | 56 | 8710 |
| (0.0000102 µg/ml) [0.000016] | 52 | 7328 |
| U1 + AZT | | |
| (10 µg/ml) [37] | 97 | 8653 |
| (1 µg/ml) [3.7] | 72 | 7898 |
| (0.1 µg/ml) [0.37] | 53 | 4363 |
| (0.01 µg/ml) [0.037] | 50 | 9626 |

TABLE 9

| Sample Identification | RT Activity (CPM) |
|---|---|
| LH70C1-4L at: [µM] | |
| 4 µg/ml [6.4] | 13,664 |
| 0.8 µg/ml [1.3] | 14,871 |
| 0.16 µg/ml [0.26] | 11,535 |
| 0.032 µg/ml [0.051] | 16,463 |
| 0.064 µg/ml [0.010] | 18,403 |
| 0.00128 µg/ml [0.0021] | 9,568 |
| 0.000256 µg/ml [0.00040] | 15,625 |
| 0.0000512 µg/ml [0.000084] | 16,937 |
| 0.0000102 µg/ml [0.000016] | 13,992 |
| AZT at: [µM] | |
| 10 µg/ml [37] | 1,990 |
| 1 µg/ml [3.7] | 1,826 |
| 0.1 µg/ml [0.37] | 2,662 |
| 0.01 µg/ml [0.037] | 1,919 |
| Infected Control (no drug) | 17,264 |
| Uninfected Control | 719 |

Results of Testing the Ability of Compound 16 to Suppress Virus Replication during an HIV-1 Infection of Primary Monocytes.

In order to determine if compound 16 suppressive activity was limited to only fresh T cells infected with HIV-1, elutriated monocytes were infected with HIV-1 and then cultured with various concentrations of compound 16 or AZT. As the data indicates in Table 10, 16 is also able to suppress HIV-1 replication in fresh elutriated monocytes. This illustrates that the effect of the drug is not only limited to T cells but also can effect virally infected monocytes.

AZT was used as a positive drug control and it inhibited HIV-1 replication in the human monocytes.

TABLE 10

| Sample Identification | p24 antigen (pg/ml) Day 17 | p24 antigen (pg/ml) Day 28 |
|---|---|---|
| 16 at: [µM] | | |
| 20 µg/ml [32] | 5 | 0 |
| 4 µg/ml [6.4] | 6 | 0 |
| 0.8 µg/ml [1.3] | 6 | 0 |
| 0.16 µg/ml [0.26] | 7 | 0 |
| 0.032 µg/ml [0.051] | 94 | 0 |

TABLE 10-continued

| Sample Identification | p24 antigen (pg/ml) Day 17 | p24 antigen (pg/ml) Day 28 |
|---|---|---|
| 0.0064 μg/ml [0.010] | 66 | 584 |
| 0.00128 μg/ml [0.0021] | 306 | 208 |
| 0.000256 μg/ml [0.00040] | 70 | 760 |
| 0.0000512 μg/ml [0.000084] | 52 | 824 |
| 0.0000102 μg/ml [0.000016] | 49 | 1536 |
| AZT at: [μM] | | |
| 10 μg/ml [37] | 0.1 | 0 |
| 1 μg/ml [3.7] | 2 | 0 |
| 0.1 μg/ml [0.37] | 5 | 0 |
| 0.01 μg/ml [0.037] | 7 | 0 |
| 0.001 μg/ml [0.0037] | 100 | 0 |
| 0.0001 μg/ml [0.00037] | 83 | 0 |
| Infected Control (no drug) | 205 | 2944 |
| Uninfected Control | 7 | 14 |

TABLE 11

| Sample Identification | P24 pg/ml −PMA | +PMA |
|---|---|---|
| ACH-2 control | 928 | 25,572 |
| ACH-2 + 16 at: [μM] | | |
| (20 μg/ml [3.2] | 1509 | 24,858 |
| (4 μg/ml [6.4] | 1194 | 23,547 |
| (0.8 μg/ml [1.3] | 976 | 20,183 |
| (0.16 μg/ml [0.26] | 1174 | 21,865 |
| (0.032 μg/ml [0.051] | 1319 | 24,650 |
| (0.064 μg/ml [0.010] | 955 | 24,364 |
| (0.00128 μg/ml [0.0021] | 811 | 22,344 |
| (0.00025 μg/ml [0.00040] | 777 | 22,756 |
| (0.0000512 μg/ml [0.000084] | 659 | 16,079 |
| (0.0000102 μg/ml [0.000016] | 666 | 17,938 |
| U1 + AZT | | |
| (10 μg/ml [37] | 939 | 16,584 |
| (1 μg/ml [3.7] | 904 | 17,088 |
| (0.1 μg/ml [0.37] | 942 | 10,621 |
| (0.01 μg/ml [0.037] | 796 | 21,373 |

Results (Table 11) from adding compound 16 to the chronically HIV-infected T cell line, ACH-2, according to methods in above examples. ACH-2 are a chronically HIV-1 infected T cell line. It was derived from A3.01 cells which is a subclone of the CEM cell line. The data below indicates the following points:

There was a 27-fold induction of virus replication when PMA was added to ACH-2 cells as compared to medium alone. This result indicates suitability for in vivo treatment of HIV infection.

Compound 16 (without PMA) did not induce the ACH-2 cells to make virus. This was also the same for AZT. These cells make a greater quantity of HIV-1 constitutively than do the U1 cells. However, there was no significant increase in the level of virus expression in the presence of either compound 16 or AZT as compared to medium alone. These are good results indicating suitability for in vivo treatment of HIV infection.

Compound 16 (with PMA) did not suppress virus replication. The results were identical to AZT. This is not surprising since AZT does not have an effect on chronically HIV infected cells (in the literature) since reverse transcription has already occurred. This data agrees with the U1 results sent earlier this week.

The various drug-treated samples were not significantly different than PMA-induced control. For there to be a significant increase, the amount of p24 antigen in the supernatant needs to increase or decrease at least 4–5 fold.

Results (Table 12) from adding Suksdorfin to Fresh Monocytes Infected with HIV-1.

The monocytes which were used for this experiment were obtained by adherence and not by elutriation; therefore, this cell population is not as pure as what was used for the 16 monocyte data above.

Suksdorfin at 20 and 4 μg/ml did suppress HIV-1 replication in fresh monocytes. This was more pronounced at day 12, which was approximately the peak of virus replication. AZT was used as the positive drug control and it was suppressive.

TABLE 12

| Sample Identification | p24 pg/ml (% suppression) | | |
|---|---|---|---|
| | Day 6 | Day 12 | Day 18 |
| Infected Control | 59,648 | 270,541 | 105,882 |
| Infected + Suksdorfin at: | | | |
| (20 μg/ml) | 16,712(72) | 25,567(91) | 23,506(78) |
| (4 μg/ml) | 48,748(18) | 89,467(67) | 103,834(0) |
| (0.8 μg/ml) | 53,043(0) | 163,656(40) | 130,970(0) |
| (0.16 μg/ml) | 70,195(0) | 203,633(0) | 125,440(0) |
| (0.032 μg/ml) | 64,614(0) | 173,998(0) | 105,882(0) |
| Infected + AZT at: | | | |
| (5 μg/ml) | 13,542 | 10,170 | 12,330 |
| (1 8,705 | 5,354 | 6,830 | |
| (0.2 μg/ml) | 34,360 | 32,778 | 31,759 |
| (0.04 μg/ml) | 23,234 | 17,144 | 22,993 |
| (0.008 μg/ml) | 42,004 | 70,380 | 75,428 |

TABLE 13

| Sample Identification | Purity | IC$_{50}$ (μg/ml) | EC$_{50}$ (μg/ml) | Therapeutic Index |
|---|---|---|---|---|
| LH70C1-4L (16) | | | | |
| +U937 cells | pure | >4 but <20 | 0.00128 | >3,125 but <15,625 |
| +PBMCs | pure | >4 but <20 | 0.018 | >222 but <1,111 |

The effect of compound 16 was tested on HIV-1 infected U937 cells and PBMCs (Table 13).

As part of efforts to biologically characterize 16 the monocytic cell line, U937 and peripheral blood mononuclear cells (PBMCs) were separately infected with HIV-1 and then had various concentrations of the analog added for 4 days of culture. As shown in table 12, there was suppression detected with both types of cellular infections.

EXAMPLE VI

Suksdorfin Analog Purification and Activity

Chemistry

Suksdorfin 1 was obtained according to Example I. Suksdorfin was also isolated previously from the roots of Angelica Morii Hayata (Shan Du Huo), a drug of folk remedy in Taiwan (Hata, et al., *Chem. Pharm. Cull.* 1974, 22, 957).

Biological Results

Suksdorfin 1 suppressed virus replication in acutely HIV-1 (IIIB isolate) infected H9 cells as presented in Example I. Compound 1 also suppressed acute HIV-1 replication in fresh peripheral blood mononuclear cells (a T cell infection) with an $EC_{50}$ value of 3.9 µM and in U937 cells (a promonocytic cell line) with an $EC_{50}$ value of 1.5 µM.

When compound 1 was added for 72 hours to the chronically HIV-1 infected T cell line, ACH-2, and to the chronically HIV-1 infected promonocytic cell line, U1, there was no increase in the induction of virus expression from either cell line. Even when both chronically HIV-1 infected cell lines were cultured in the presence of a known virus inducer such as the phorbol ester, PMA (phorbol 12-myristate 13-acetate), there was no alteration in the level of virus expression (Table 3). In addition, compound 1 was found to potentiate the anti-HIV effects of three nucleosides AZT, ddi, and ddc. Combination of 4 µg/ml of 1 with these nucleosides reduced their $EC_{50}$ values by 40-fold (for ddc), 400-fold (for AZT), and 4000-fold (for ddi) (Table 15).

As shown in Table 1, only 1 showed potent anti-HIV-1 activity at nontoxic concentrations. All other compounds (2–11) were either inactive or were less active and more toxic. The furanocoumarins (3–10) were inactive or active only at toxic concentrations (e.g., the therapeutic index of 4 was 1.3). The dicoumaryl ether 11 showed no activity.

Discussion

The inhibition of virus replication mediated by suksdorfin 1 in both T (H9) and promonocytic (U937) cell line acute HIV-1 infections designates this compound as a lead structure in a new class of potential anti-HIV agents. To further demonstrate suksdorfin's broad cellular specificity and potential clinical relevance, HIV-1 replication in fresh PHA-stimulated PBMCs (T cell) was found also to be suppressed in its presence The absence of increased levels of viral replication in chronically infected cells treated with compound 1 suggests that it would not increase the in vivo replication of HIV in a patient who is latently infected. The synergistic effects of compound 1 with the reverse transcriptase inhibitors AZT, ddi, and ddc are significant results demonstrating that compound 1 and analogs accord to formulae (I)–(XX) are expected to have increased anti-HIV activity and/or decreased toxicity of these known nucleoside drugs. In the preliminary structure-activity relationship study, the 4'-isovaleryl group of 1 was important for selective HIV-1 inhibition. Replacement of this group with an angeloyl moiety as in pteryxn compound 2 increased the toxicity by -fold and slightly reduced anti-HIV-1 activity.

In summary, suksdorfin analogs as compounds according to formulae (I)–(XX) are expected to be useful for chemotherapy of HIV infection and/or AIDS, either alone or in combination with FDA-approved nucleosides. Preliminary in vitro results have shown good anti-HIV activities in a variety of cell lines.

Experimental Section
Chemistry

Isolation of Suksdorfin as presented herein, in Examples I–VI, The *Lomatium suksdorfii* plant used was collected in Washington state. The ground, air-dried fruits (100 g) were extracted with MeOH. The active MeOH extract was partitioned between hexane and 90% MeOH (1:1). Evaporation of the active hexane extract gave a crystalline residue. Recrystallization of this residue with hexane yielded 1 as colorless needles (1 g, 1% yield): mp 140–141°; $[\alpha]D^{24}$ +4° (c 0.5, EtOH). The IR and NMR data of compound 1 are identical to those reported (Willette, et al. *J. Pharm. Sci.* 1962, 51, 149) (Hata, et al., *Chem. Pharm. Cull.* 1974, 22, 957) for suksdorfin, which was previously isolated from this same species.(Willette, et al. *J. Pharm. Sci.* 1962, 51, 149)

Suksdorfin-related Coumarins

Compounds 2 (pteryxin), (Lee, et al., *J. Pharm. Sci.* 1968, 57, 865) 3 (columbianadin), (Soine, et al., *J. Pharm. Sci.* 1967, 56, 655) (Willette, et al. *J. Pharm. Sci.* 1964, 53, 275) 4 (nodakenetin), (Lee, et al., *J. Pharm. Sci.* 1969, 58, 675) 5 (nodakenin), (Lee, et al., *J. Pharm. Sci.* 1969, 58, 675) 6 (acetyl nodakenin), (Lee, et al., *J. Pharm. Sci.* 1969, 58, 675) 7 (imperatorin), (Lee, et al., *J. Pharm. Sci.* 1969, 58, 675) 8 (bergapten), (Lee, et al., *J. Pharm. Sci.* 1969, 58, 681) 9 (isoimperatorin), (Lee, et al., *J. Pharm. Sci.* 1969, 58, 675) 10 (oxypeucedanin), (Lee, et al., *J. Pharm. Sci.* 1969, 58, 675) and 11 (daphnoretin) (Lee, et al., *J. Nat. Prod.* 1981, 44, 530) were obtained according to published methods.

Biology

Chronically HIV-1 infected cell lines. HIV-1 chronically infected T cell line, ACH-2[12], and HIV-1 chronically infected promonocytic cell line, U1 13, were continuously maintained in RPMI 1640 with 10% fetal calf serum (FCS). For experiments, the cell lines were only used in the low phase of growth. Cells ($0.5 \times 10^6$ cells/well) and either various concentrations of suksdorfin or medium alone were added to 24-well plates in the presence or absence of PMA ($10^{-8}$M). After 72 hours at 37° C. and 5% $CO_2$, an aliquot of the cell-free supernatants were collected and analyzed for p24 antigen by ELISA (see below for details of p24 antigen ELISA).

HIV Growth Inhibition Assay

The T cell line, H9, and the promonocytic cell line, U937, were maintained separately in continuous culture with complete medium (RPMI 1640 and 10% fetal calf serum (FCS) at 5% $CO_2$ and 37° C. Cell lines were used in experiments only when in log phase of growth; whereas, uninfected peripheral blood mononuclear cells (PBMCs) were first stimulated with PHA (1 µg/ml) for 3 days. All cell targets were incubated with HIV-1 (IIIB isolate, $TCID_{50}$ $10^4$ IU/ml, at a multiplicity of infection of 0.1–0.01 IU/cell) for 1 hour at 37° C. and 5% $CO_2$. The cell lines and PBMCs were washed thoroughly to remove unabsorbed virions and resuspended at $4 \times 10^5$ cells/ml in complete medium or complete medium with 10% v/v interleukin (Pettinato, et al. *J. Amer. Pharm. Asso.* 1959, 48,423) IL-2, respectively. Aliquots (1 ml) were placed in wells of 24-well culture plates containing an equal volume of test compound (diluted in the appropriate culture medium). After incubation for 4 days at 37° C., cell density of uninfected cultures was determined by counting cells in a Coulter counter to assess toxicity of the test compound. A p24 antigen ELISA assay was used to determine the level of virus released in the medium of the HIV-infected cultures. The p24 antigen assay uses a HIV-1 anti-p24 specific monoclonal antibody as the capture antibody coated-on 96-well plates. Following a sample incubation period, rabbit serum containing antibodies for HIV-1 p24 is used to tag any p24 "captured" onto the microtiter well surface. Peroxidase conjugated goat anti-rabbit serum is then used to tag HIV-1 p24 specific rabbit antibodies which have complexed with captured p24. The presence of p24 in test samples is then revealed by addition of substrate. The cut-off for the p24 ELISA assay is 12. pg/ml. P24 in the culture medium was quantitated against a standard curve containing known amounts of p24. The effective ($EC_{50}$) and inhibitory ($IC_{50}$) concentrations (for anti-HIV activity and cytotoxicity, respectively) were determined graphically. Both the $EC_{50}$ and $IC_{50}$ values were calculated by plotting drug concentration versus percent inhibition, and then identifying a 50% inhibition value from the graph.

Combination Study

The experimental design is identical to the growth inhibition assay except that various concentrations of AZT, ddI or ddC were also added to cultures of acutely HIV-1 infected H9 cells that either have or have no received different concentrations of suksdorfin. The concentrations of AZT, ddI and ddC were 5 ten-fold dilutions starting at 1 µg/ml.

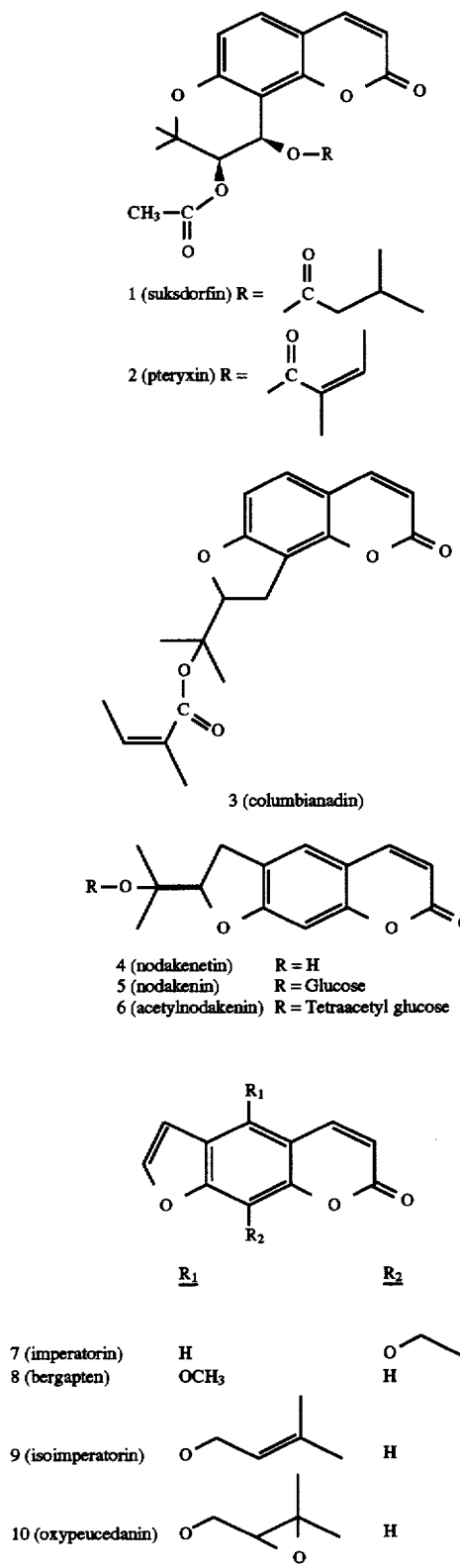
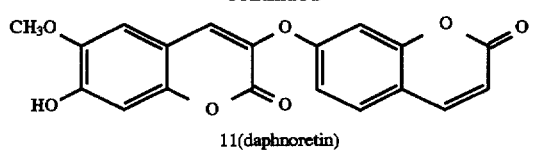

11(daphnoretin)

TABLE 14

HIV Inhibition of HIV-1 Replication in H9 Lymphocytes by Suksdorfin 1 and Related Compounds 2-11.

| Compound | $IC_{50}$ (µM)[a] | $IC_{50}$ (µM)[b] | Therapeutic Index |
|---|---|---|---|
| 1 Suksdorfin | >52.0 | 1.3 | >40.) |
| 2 Pteryxin | >10.4 | 4.6 | >3.7 |
| 3 Columbianadin | >6.1 | 4.6 | >1.3 |
| 4 Nodakenetin | ND[c] | Inactive[d] | ND |
| 5 Nodakenin | ND | Inactive | ND |
| 6 Acetyl Nodakenin | ND | Inactive | ND |
| 7 Ipratorin | >84.1 | 11.1 | >6.7 |
| 8 Bergapten | >92.6 | 30.1 | >3.1 |
| 9 Isoimperatorin | >185.2 | 40.7 | >4.6 |
| 10 Oxypeucedanin | >69.9 | 31.5 | >2.2 |
| 11 Daphnoretin | ND | Inactive | ND |

[a]Concentration which inhibits uninfected cell growth by 50%
[b]Concentration which inhibits viral replication by 50%
[c]ND = not determined
[d]No suppression of HIV-1 replication in H9 cells

TABLE 15

Inhibition of HIV-1 Replication in ACH-2 and U1 Cells by Suksdorfin 1

| Suksdorfin | ACH-2 Cells | | U1 Cells | |
|---|---|---|---|---|
| Concentration | -PMA | +PMA | -PMA | +PMA |
| 0 µg/ml | 3,676 pg/ml | 52,122 pg/ml | 0 pg/ml | 6,963 pg/ml |
| 20 µg/ml | 4,541 pg/ml | 49,914 pg/ml | 0 pg/ml | 5,096 pg/ml |
| 4 µg/ml | 4,723 pg/ml | 61,235 pg/ml | 0 pg/ml | 9,728 pg/ml |
| 0.8 µg/ml | 3,821 pg/ml | 55,910 pg/ml | 0 pg/ml | 7,360 pg/ml |
| 0.16 µg/ml | 3,688 pg/ml | 50,775 pg/ml | 0 pg/ml | 6,611 pg/ml |

[a]Chronically HIV-1 infected T cell line
[b]Chronically HIV-1 infected promonocytic cell line
[c]p24 antigen level after 72 hours in culture
[d]PMA $10^{-8}$ M

TABLE 16

Inhibition of HIV-1 replication in H9 Lymphocytic Cells by Combination of Suksdorfin 1 and ATZ, ddI, and ddC.

| Compound | $IC_{50}$ (µM)[a] | $IC_{50}$ (µM)[b] | Therapeutic Index |
|---|---|---|---|
| Suksdorfin | >4 but <20 | 2.8 | >1.4 but <7.1 |
| AZT | >1 | 0.04 | >25 |
| ddI | >1 | 0.4 | >2.5 |
| ddC | >1 | 0.004 | >250 |
| 4 µg/ml Suksdorfin + AZT | >1 | <0.0001 | >10,000 |
| 4 µg/ml Suksdorfi + ddI | >1 | <0.0001 | >10,000 |
| 4 µg/ml Suksdorfin + ddC | >1 | <0.0001 | >10,000 |

[a]Concentration which inhibits uninfected cell growth by 50%
[b]Concentration which inhibits viral replication by 50%

EXAMPLE VII

Suksdorfin Analog Synthesis and Activity

Recently, much effort has been focused on the search for compounds effective in the inhibition of HIV, the etiologic agent of AIDS. The result has been the identification of numerous inhibitors of HIV reverse transcriptase (RT) nd HIV protease. These include nucleoside analogs and peptide mimics, respectively. Although the RT inhibitors, such as AZT, ddI, and ddC, are available as anti-AIDS drugs, their clinical effectiveness i limited by their toxicity as well as the development of drug resistant virus. The discovery and development of a new class of anti-HIV agents with structures and mechanisms of action different from those of nucleoside analogs mentioned above are of current interest.

In the course of our continuing search for novel anti-HIV agents from natural products, suksdorfin compound 1 was isolated as an active principle from the fruits of *Lomatium suksdorfii* (Umbelliferae) e.g., as presented in Example VI. Compound 1 exhibited inhibitory activity against HIV-1 replication in acutely infected H9 lymphocytes with an $EC_{50}$ value of 1.3 µM and a therapeutic index of >40. Moreover, compound 1 was found to demonstrate a synergistic effect against HIV replication when it was co-administered with either AZT, ddI, or ddC (data not shown). This discovery has prompted our synthesis of the dihydroseselin type pyranocoumarin derivatives (compounds 2–5) as a new class of anti-HIV agents.

The synthesis of 2–5 is shown in Scheme 1 as present in Example IV. Seselin compound 7 was prepared from the commercially available 7-hydroxycoumarin 6 according to a procedure reported in the literature. (Hlubuek, et al., *Aust. J. Chem.*, 1971, 62, 2347–2354) Subsequent oxidation (El-Antably, et al., *J. Pharm. Sci.*, (1973) 62 1643–1648) of compound 7 with $OSO_4$ gave the racemic cis-khellactone compound 8. Alternatively, compound 7 was treated with m-chloroperbenzoic acid (Schroeder, et al., *Chem. Ber.*, 1959, 93, 2388-2363) to furnish 4'—O—m-chlorobenzoyl-(+/−)-trans-khellactone 9, which was then hydrolyzed to produce the racemic trans-khellactone 10. Treatment of 8 and 10 with (−)-camphanoyl chloride (Gerlach, et al., *J. Chem. Soc., Chem. Commun.*, 1973, 274–275) afforded diastereoisomers in each case. The diastereoisomers were separated by repeated column chromatography to yield four isomers of di—O—(−)-campanoylkhellactone (2–5).

The stereochemistries of 2–5 were assigned as follows: the naturally occurring di—O—acyl-(+)-cis-khellactone (e.g., 11) was hydrolyzed with base to give (+)-cis-11 as well as (−)-trans-12 khellactones. (Willette, et al., *J. Pharm. Sci.* 1962, 51, 149–156) Treatment of 11 and 12 with (−)-camphanoyl chloride afforded their corresponding diesters, which were found to be identical with 2 and 4, respectively, by direct spectral comparison (Scheme 3).

As shown in Table 17, compound 2 demonstrated extremely potent inhibitory activity against HIV-1 replication in acutely infected H9 lymphocytes with an $EC_{50}$ value of 0.00041 µM. The $IC_{50}$ range against uninfected H9 cell growth was >32 but <160 µM, which was less toxic than the active principle (compound 1). The therapeutic index for 2 was >78,049 but <390,244. Since the $EC_{50}$ value and the therapeutic index of AZT in this assay system are 0.15 µM and 12,500, respectively, compound 2 is more potent than AZT as an anti-HIV agent.

Compound 3, the diastereoisomer of 2, as well as the trans-khellactone derivatives with same acyl groups (4 and 5) showed much less anti-HIV activity than 2. Since only 1 and 2 show potent anti-HIV activity and both contain the same configuration at C-3' and C-4', the (+)-cis-khellactone skeleton can be required for the enhanced anti-HIV activity.

In order to determine whether the anti-HIV activity of 2 was limited to acute HIV-1 infections of the T cell line, H9, both PHA-stimulated peripheral blood mononuclear cells (PBMCs) and the promonocytic cell line, U937, were separately infected with HIV-1. The results showed that there was suppression detected no matter which type of target cell was used. This indicates that compound 2 was an effective suppressor of virus replication no matter if fresh T cells (PBMCs) or a T cell line (H9) was used or a monocytic cell (U937) was infected with HIV-1. The $EC_{50}$ value and the therapeutic index against PBMCs were 0.029 µM and >222 but <1,111, while those against U937 were 0.0021 µM and >3,125 but <15,625.

Studies on the mechanism of action for 1, 2 and other related compounds are in progress.

In conclusion, compound 2 and its related compounds, such as 1, represent a new class of potent anti-HIV agents, which are structurally unique compared with other known anti-AIDS drugs.

TABLE 17

HIV Infection by Di-O-(−)-camphanoylkhellactones (2–5), Suksdorfin 1, and AZT

| Compounds | $IC_{50}$ (µM) | $EC_{50}$ (µM) | Therapeutic Index |
|---|---|---|---|
| 2 | >32 but <160 | 0.00041 | >78,049 but <390,244 |
| 3 | 1,700 | 51 | >33.3 |
| 4 | >6.4 but <32 | >6.4 but <32 | |
| 5 | >32 | 32 | >1 |
| Suksdorfin 1 | >52 | 1.3 | >40 |
| AZT | 1,875 | 0.15 | 12,500 |

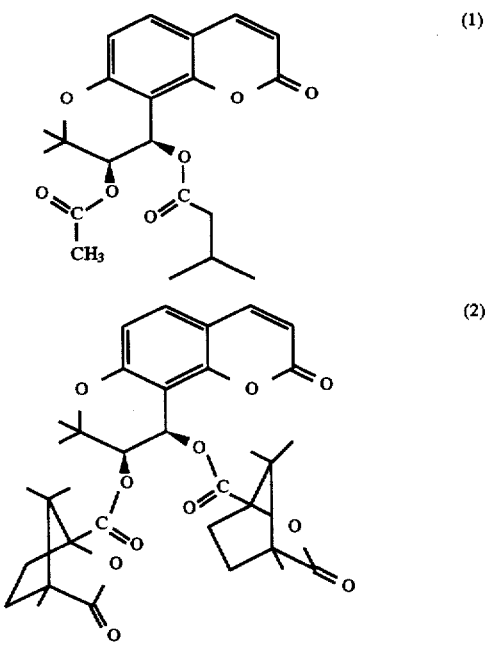

45
-continued
(3)
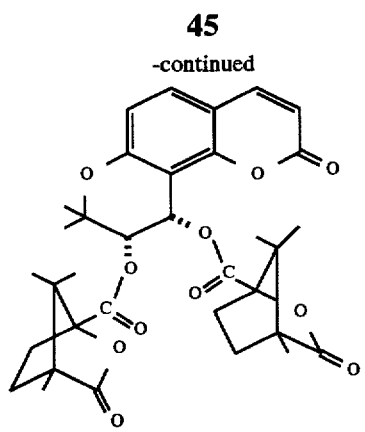
(4)
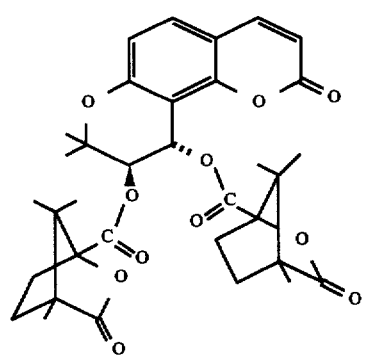
46
-continued
(5)
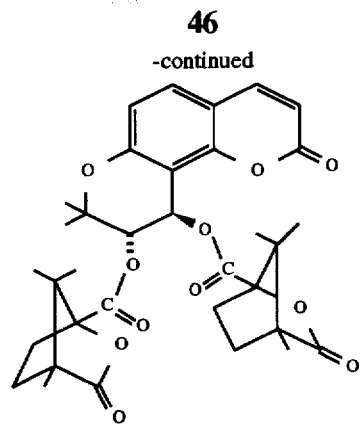
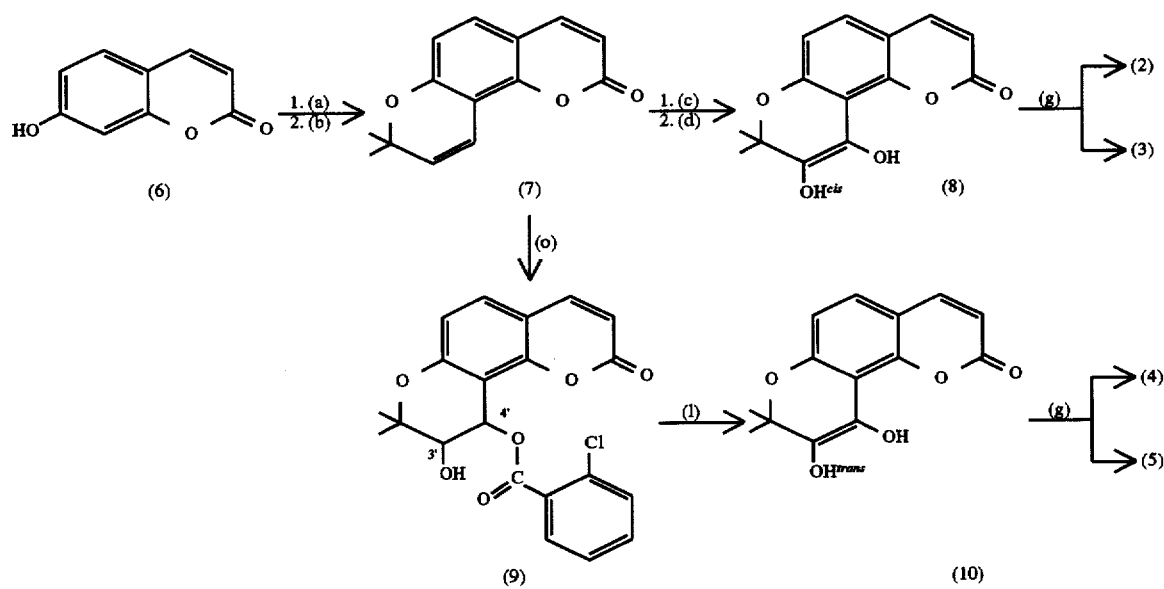
Synthesis of 3', 4'-Di-O-Camphanoylkhellactones (2–5)
(a) 3-Chloro-3-methylbut-1-yne, KI, $K_2CO_3$ in acetone (b) diethylanilino, reflux
(c) $OsO_4$, dioxane (d) $NaHSO_3$ (o) m-chloroperbenzoic acid, $CHCl_3$ (l) 0.5 N KOH-dioxane
(g) (−)-camphanoyl chloride, pyridine

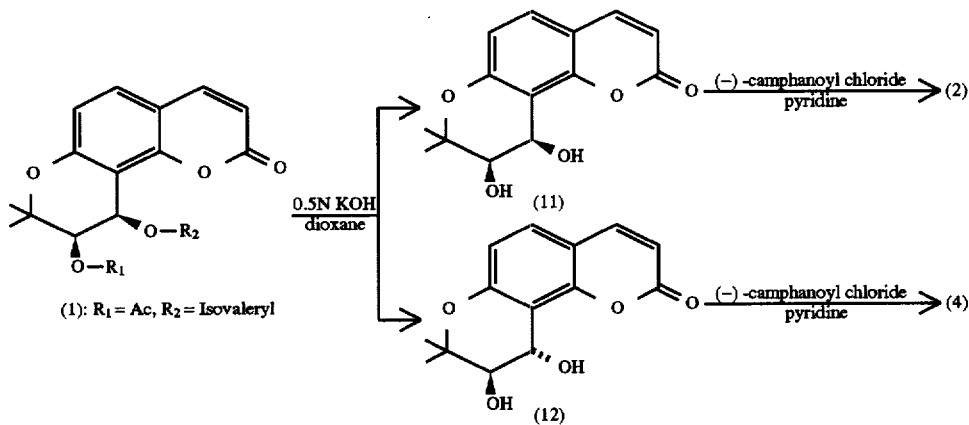

Scheme 20

Detailed Analytical Data for 2-5

3',4'-Di—O—(−)-Camphanoyl-(+)-cis-Khellactone (2): Colorless needles (from EtOH); mp 200°–202° C; [α]D/20°+31.1° (c=0.5, CHCl₃); Positive FAB MS m/z 623 (M+H)+, 425 (M-camphanic acid)+, 227 (M-2xcamphanic acid)+; IR (KBr) 1790, 1745 (COO), 1605 (C+C); 1H NMR (300 MHz, CDCl₃ ? 7.62 (1H, d, J=9.5 Hz, H-4), 7.41 (1H, d, J=8.5 Hz, H-5), 6.82 (1H, d, J=8.5 Hz, H-6), 6.66 (1H, d, J=5 Hz, H-4'), 6.24 (1H, d, J=9.5 Hz, H-3), 5.39 (1H, d, J=5 Hz, H-3'), 2.50, 2.23, 1.94, 1.70 (each 2H, m, camphanoyl CH₂), 1.50, 1.45 (each 3H, s, 2'-CH₃), 1.12, 1.11, 1.10, 1.08, 1.01, 0.98 (each 3H, s, camphanoyl CH₃). Anal. Calcd for C₃₄H₃₈O₁₁:CF, 65.58; H, 6.15. Found: C, 65.41; H, 6.21.

3',4'-Di—O—(−)-Camphanoyl-(−)-cis-Khellactone (3): Colorless needles (from EtOH); mp242°–244° C.; [α]D/20°–67.7° (c=0.5, CHCl₃); Positive FAB MS m/z 623 (M+H)+, 425 (M-camphanic acid)+, 227 (M-2xcamphanic acid)+; IR (KBr) 1780, 1750 (COO), 1605 (C=C); 1H NMR (300 MHz, CDCl₃ ? 7.61 (1H, d, J=9.5 Hz, H-4), 7.40 (1H, d, J=8.5 Hz, H-5), 6.82 (1H, d, J=8.5 Hz, H-6), 6.74 (1H, d, J=4.5 Hz, H-4'), 6.22 (1H, d, J=9.5 Hz, H-3), 5.47 (1H, d, J=4.5 Hz, H-3'), 2.55, 2.34, 2.10, 1.93, 1.70 (8H in total, each m, camphanoyl CH₂), 1.56, 1.45 (each 3H, s, 2'-CH₃), 1.13, 1.12, 1.06, 1.04, 0.94 (18H in total, each s, camphanoyl CH₃). Anal. Calcd for C₃₄H₃₈O₁₁:CF, 65.58; H. 6.15. Found: C, 65.46; H, 6.12.

3',4'-Di—O—(−)-Camphanoyl-(−)-trans-Khellactone (4): Colorless needles (from EtOH); mp249°–251° C.; [α]D/20°+18.4° (c=0.5, CHCl₃); Positive FAB MS m/z 623 (M+H)+, 425 (M-camphanic acid)+, 227 (M-2xcamphanic acid)+; IR (KBr) 1790, 1770, 1750 (COO), 1610 (C=C); 1H NMR (300 MHz, CDCl₃) ? 7.63 (1H, d, J=9.5 Hz, H-4), 7.42 (1H, d, J=8.5 Hz, H-5), 6.86 (1H, d, J=8.5 Hz, H-6), 6.30 (1H, d, J=3.5 Hz, H-4'), 6.24 (1H, d, J=9.5 Hz, H-3), 5.39 (1H, d, J=3.5 Hz, H-3'), 2.50, 2.46, 2.07, 1.93, 1.66 (8H in total, each m, camphanoyl CH₂), 1.50, 1.41 (each 3H, s, 2'-CH₃), 1.12, 1.09, 1.08, 1.00, 0.98, 0.97 (each 3H, s, camphanoyl CH₃). Anal. Calcd for C₃₄H₃₈O₁₁:CF, 65.58; H, 6.15. Found: C, 65.60; H, 6.17.

3',4'-Di—O—(−)-Camphanoyl-(+)-trans-Khellactone (5): Colorless needles (from EtOH); mp253°–254° C.; [α]D/20°–42.0° (c=0.5, CHCl₃); Positive FAB MS m/z 623 (M+H)+, 425 (M-camphanic acid)+, 227 (M-2xcamphanic acid)+; IR (KBr) 1800, 1750, 1735, (COO), 1605 (C=C); 1H NMR (300 MHz, CDCl₃) ? 7.64 (1H, d, J=9.5 Hz, H-4), 7.41 (1H, d, J=8.5 Hz, H-5), 6.84 (1H, d, J=8.5 Hz, H-6), 6.29 (1H, d, J=3.5 Hz, H-4'), 6.26 (1H, d, J=9.5 Hz, H-3), 5.40 (1H, d, J=3.5 Hz, H-3'), 2.49, 2.12, 1.92, 1.68 (each 2H, m, camphanoyl CH₂), 1.50, 1.41 (each 3H, s, 2'-CH₃), 1.10, 1.09, 1.07, 1.06, 0.99, (18H in total, each s, camphanoyl CH₃). Anal. Calcd for C₃₄H₃₈O₁₁:CF, 65.58; H, 6.15. Found: C, 65.66; H, 6.19.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

What is claimed is:
1. A compound having the formula:

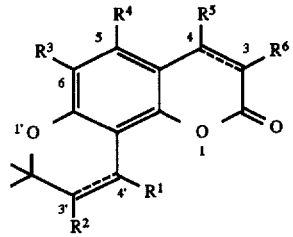

wherein $R^1$, $R^2$ are cis-β, cis-α, trans-3'-α or trans-3'-β oriented, and wherein $R^1$, $R^2$, $R^3$ and $R^4$ are H, $C_{1-10}$ alkyl $C_{1-10}$ O-acyl, O-alkyl, O-camphanoyl, amide, or $CH_2COOR'$, where R' is $C_{1-10}$ alkyl;

$R^5$ is H, $C_{1-10}$ alkyl, $C_{1-10}$ acyl, $CF_3$, amide or $CH_2COOR^7$, where $R^7$ is $C_{1-10}$ alkyl; and $R^6$ is H, halogen, $C_{1-10}$ alkyl, or $-CH_2CH_2NR^7R^8$, where $R^8$ is $C_{1-10}$ alkyl, and wherein C3' and C4', and C3 and C4, may be bound by a single or a double bond; provided that when $R^3$, $R^4$, $R^5$ and $R^6$ are H, then (a) $R^1$ and $R^2$ are not both $C_{1-10}$ O-acyl, and
(b) $R^1$ or $R^2$ cannot be $C_{1-4}$ O-alkyl when the other of $R^1$ or $R^2$ is $C_{1-10}$ O-acyl.

2. A phamceutical composition comprising a compound according to claim 1, or a pharmaceutically acceptable ester, ether, sulfate, carbonate, glucuronide or salt thereof, and a pharmaceutically acceptable carrier.

3. A method for inhibiting a retroviral infection in cells or tissue of an animal, comprising
administering an effective retroviral inhibiting amount of a pharmaceutical composition, said composition comprising a compound according to Formula I;

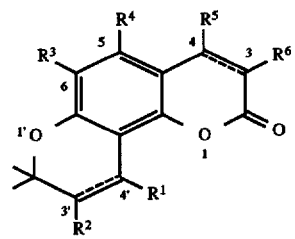

or a pharmaceutically acceptable ester, ether, sulfate, carbonate, glucuronide or salt thereof, and a pharmaceutically acceptable carrier, wherein $R^1$, $R^2$ are cis-β, cis-α, trans-3'-α or trans-3'-β oriented, and wherein $R^1$, $R^2$, $R^3$ and $R^4$ are H, $C_{1-10}$ alkyl $C_{1-10}$ O-acyl, O-camphanoyl, O-alkyl, amide, or $CH_2COOR'$, where R' is $C_{1-10}$ alkyl;

$R^5$ is H, $C_{1-10}$ alkyl, $C_{1-10}$ acyl, $CF_3$, amide or $CH_2COOR^7$, where $R^7$ is $C_{1-10}$ alkyl; and $R^6$ is H, halogen, $C_{1-10}$ alkyl, or $-CH_2CH_2NR^7R^8$, where $R^8$ is $C_{1-10}$ alkyl, and wherein C3' and C4', and C3 and C4, may be bound by a single or a double bond.

4. The method of claim 3, wherein said composition is administered to provide said compound in an amount ranging from 0.1 to 100 mg/kg body weight.

5. A method for treating a patient suffering from a retroviral related pathology, comprising administering to said patient an effective retroviral inhibiting amount of a pharmaceutical composition, said composition comprising a compound according to Formula I:

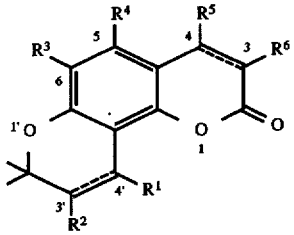

or a pharmaceutically acceptable ester, ether, sulfate, carbonate, glucuronide or salt thereof, and a pharmaceutically acceptable carrier, wherein $R^1$, $R^2$ are cis-β, cis-α, trans-3'-α or trans-3'-β oriented, and wherein $R^1$, $R^2$, $R^3$ and $R^4$ are H, $C_{1-10}$ alkyl $C_{1-10}$ O-acyl, O-alkyl, O-camphanoyl, amide, or $CH_2COOR'$, where R' is $C_{1-10}$ alkyl;

$R^5$ is H, $C_{1-10}$ alkyl, $C_{1-10}$ acyl, $CF_3$, amide or $CH_2COOR^7$, where $R^7$ is $C_{1-10}$ alkyl; and $R^6$ is H, halogen, $C_{1-10}$ alkyl, or $-CH_2CH_2NR^7R^8$, where $R^8$ is $C_{1-10}$ alkyl, and wherein C3' and C4', and C3 and C4, may be bound by a single or a double bond.

6. A compound according to claim 1, wherein $R^1$ is $OCOCH_2CH(CH_3)_2$, $R^2$ is $OCOCH_3$ and $R^3$, $R^4$, $R^5$ and $R^6$ are H.

7. A compound according to claim 1, wherein C3 and C4 are bound by a double bond.

8. A compound according to claim 7, wherein $R^3$, $R^4$, $R^5$ and $R^6$ are H.

9. A compound according to claim 1, wherein $R^5$ is $C_{1-10}$ alkyl, $CF_3$ or $CH_2COOR^7$, and $R^7$ is a $C_{1-10}$ alkyl.

10. A compound according to claim 1, wherein $R^6$ is H, halogen or $CH_2CH_2NR^7R^8$ where $R^7$ and $R^8$ are the same or different $C_{1-10}$ alkyl.

11. A compound according to claim 1, wherein said compound is selected from the group consisting of (I-B), (I-C), (I-D), (I-F), (I-G), (I-H), (I-J), (I-K), (I-L), (I-M), (I-P), (I-S), (I-T), (I-U), (I-V), (I-W), (I-Y), and (I-Z).

12. A compound according to claim 1, wherein said compound is (I-P).

13. A compound according to claim 1, wherein $R^3$, $R^4$, $R^5$ and $R^6$ is hydrogen, and wherein $R^1$ and $R^2$ are both

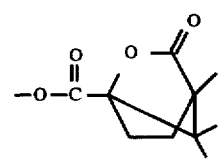

14. A compound according to claim 1 wherein $R^1=R^2=$

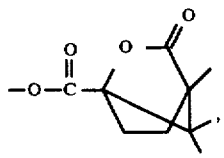

$R^3=R^4=H$, $R^5=CH_3$ and $R^6=H$ or Cl.

15. A compound according to claim 14 wherein $R^6$ is H.

16. A pharmaceutical composition according to claim 2, further comprising a drug selected from an antiviral agent or an immunostimulating agent.

17. A composition according to claim 16, wherein said antiviral agent is selected from the group consisting of gamma globulin, amantadine, guanidine, hydroxybenzimidazole, interferon-α, interferon-β, interferon-γ, thiosemicarbazones, methisazone, rifampin, ribavirin, a pyrimidine analog, a purine analog, foscarnet, phosphonoacetic acid, acyclovir, dideoxynucleosides, and ganciclovir.

18. The method of claim 4, wherein said composition is administered to provide said compound in an amount ranging from 1 to 100 mg/kg.

19. The method of claim 3, wherein said animal is selected from the group consisting of mammals and birds.

20. The method of claim 19, wherein said mammal is a human.

21. The method according to claim 3 wherein $R^1$ is $OCOCH_2CH(CH_3)_2$, $R^2$ is $OCOCH_3$ and $R^3$, $R^4$, $R^5$ and $R^6$ are H.

22. The method according to claim 21, wherein C3 and C4 are bound by a double bond.

23. The method according to claim 3, wherein said compound is selected from the group consisting of (I-A), (I-B), (I-C), (I-D), (I-E), (I-F), (I-G), (I-H), (I-J), (I-K), (I-L), (I-M), (I-N), (I-O), (I-P), (I-Q), (I-R), (I-S), (I-T), (I-U), (I-V), (I-W), (I-X), (I-Y), and (I-Z).

24. A method according to claim 3, wherein $R^1$ and $R^2$ are

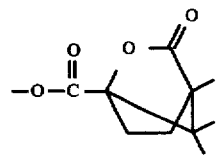

$R^3$ and $R^4$ are both hydrogen, $R^5$ is methyl and $R^6$ is one of hydrogen or chlorine.

25. A compound having the formula:

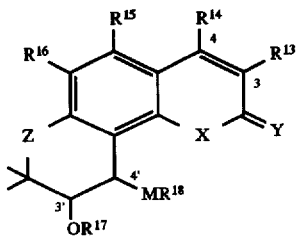

wherein
M is O or NH;
X and Z are O;
Y is O, NH or S;
$R^{13}$, $R^{14}$, $R^{15}$ and $R^{16}$ are independently hydrogen, halogen, hydroxy, alkoxy, acyloxy, amino, monoalkylamino, dialkylamino, trifluoromethyl, trifluoromethoxy or —CH$_2$CONH-alkyl;

$R^{17}$ and $R^{18}$ are independently hydrogen, $C_{1-10}$ alkyl, $C_{1-10}$ acyl, camphanoyl, aryl, trifluoromethylcarbonyl, amide or —CH$_2$COOR$^{19}$, where $R^{19}$ is $C_{1-10}$ alkyl or aryl; and where the configurations at 3' or 4' can be (R) or (S); and $R^{17}$ and $R^{18}$ can be oriented cis-β, cis-α, trans-3'-β or trans-3'-α;

with the proviso that
when M, X, Y and Z are each O and $R^{13}$, $R^{14}$, $R^{15}$ and $R^{16}$ are each hydrogen,
then $R^{17}$ or $R^{18}$ are each other than hydrogen, $C_{1-10}$ acyl or $C_{1-10}$ alkyl.

26. A compound according to claim 25, wherein X, M, Y and Z are each oxygen;
and $R^{17}$ and $R^{18}$ are both (+)-camphanoyl or (−)-camphanoyl.

27. A pharmaceutical composition comprising a compound according to claim 25, or a pharmaceutically acceptable ester, ether, sulfate, carbonate, glucuronide or sale thereof, and a pharmaceutically acceptable carrier.

28. A pharmaceutical composition according to claim 27, further comprising a drug selected from an antiviral agent or an immunostimulating agent.

29. A composition according to claim 27, wherein said antiviral agent is selected from the group consisting of gamma globulin, amantadine, guanidine, hydroxybenzimidazole, interferon-α, interferon-β, interferon-γ, thiosemicarbazones, methisazone, rifampin, ribavirin, a pyrimidine analog, a purine analog, foscarnet, phosphonoacetic acid, acyclovir, dideoxynucleosides and ganciclovir.

30. A method for inhibiting a retroviral infection in cells or tissue of an animal, comprising administering an effective retroviral inhibiting amount of a compound according to formula (III):

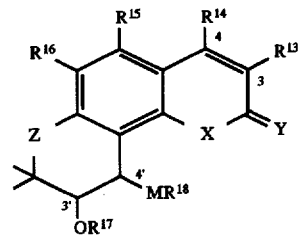

wherein
M is O or NH;
X and Z are O;
Y is O, NH or S;
$R^{13}$, $R^{14}$, $R^{15}$ and $R^{16}$ are independently hydrogen, halogen, hydroxy, alkoxy, acyloxy, amino, monoalkylamino, dialkylamino, trifluoromethyl, trifluoromethoxy or —CH$_2$CONH-alkyl;

$R^{17}$ and $R^{18}$ are independently hydrogen, $C_{1-10}$ alkyl, $C_{1-10}$ acyl, camphanoyl, aryl, trifluoromethylcarbonyl, amide, or —CH$_2$COOR$^{19}$, where $R^{19}$ is $C_{1-10}$ alkyl or aryl, and where the configurations at 3' or 4' can be (R) or (S); and $R^{17}$ and $R^{18}$ can be oriented cis-β, cis-α, trans-3'-β or trans-3'-α.

31. The method according to claim 30, wherein X, M, Y and Z are each oxygen and $R^{17}$ and $R^{18}$ are both (+)-camphanoyl or (−)-camphanoyl.

32. A method for treating a patient suffering from a retroviral related pathology, comprising administering to said patient an effective retroviral inhibiting mount of a compound according to formula (III):

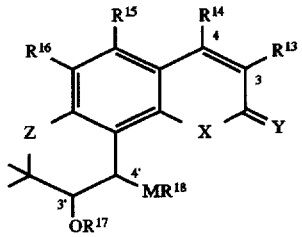

wherein

M is O or NH;

X and Z are O;

Y is O, NH or S;

$R^{13}$, $R^{14}$, $R^{15}$ and $R^{16}$ are independently hydrogen, halogen, hydroxy, alkoxy, acyloxy, amino, monoalkylarnino, dialkylamino, trifluoromethyl, trifluoromethoxy or —$CH_2CONH$-alkyl;

$R^{17}$ and $R^{18}$ are independently hydrogen, $C_{1-10}$ alkyl, $C_{1-10}$ acyl, aryl, trifluoromethylcarbonyl, carbamoyl, camphanoyl, or —$CH_2COOR^{19}$, where $R^{19}$ is $C_{1-10}$ alkyl or aryl, and where the configurations at 3' or 4' can be (R) or (S); and $R^{17}$ and $R^{18}$ can be oriented cis-β, cis-α, trans-3'-β or trans-3'-α.

* * * * *